(12) United States Patent
Groves

(10) Patent No.: US 8,232,267 B2
(45) Date of Patent: Jul. 31, 2012

(54) PORPHYRIN CATALYSTS AND METHODS OF USE THEREOF

(75) Inventor: John T. Groves, Princeton, NJ (US)

(73) Assignee: The Trustees of Princeton University, Princeton, NJ (US)

(*) Notice: Subject to any disclaimer, the term of this patent is extended or adjusted under 35 U.S.C. 154(b) by 249 days.

(21) Appl. No.: 12/311,640

(22) PCT Filed: Oct. 5, 2007

(86) PCT No.: PCT/US2007/021445
§ 371 (c)(1),
(2), (4) Date: Dec. 23, 2009

(87) PCT Pub. No.: WO2008/094222
PCT Pub. Date: Aug. 7, 2008

(65) Prior Publication Data
US 2010/0093688 A1 Apr. 15, 2010

Related U.S. Application Data

(60) Provisional application No. 60/850,179, filed on Oct. 6, 2006.

(51) Int. Cl.
*A01N 55/02* (2006.01)
*A01N 43/36* (2006.01)
*A61K 31/40* (2006.01)
*C07B 47/00* (2006.01)
*C07D 487/22* (2006.01)

(52) U.S. Cl. .................. 514/185; 514/410; 540/145

(58) Field of Classification Search .................. 540/145; 514/185, 410
See application file for complete search history.

(56) References Cited

U.S. PATENT DOCUMENTS

| | | |
|---|---|---|
| 3,710,795 A | 1/1973 | Higuchi et al. |
| 5,109,016 A | 4/1992 | Dixon et al. |
| 5,262,564 A | 11/1993 | Kun et al. |
| 5,284,647 A | 2/1994 | Niedballa et al. |
| 5,622,933 A | 4/1997 | Sabatier et al. |
| 5,663,393 A | 9/1997 | Jacobsen et al. |
| 5,714,166 A | 2/1998 | Tomalia et al. |
| 5,801,229 A | 9/1998 | Sessler et al. |
| 6,002,026 A | 12/1999 | Groves et al. |
| 6,060,478 A | 5/2000 | Gilligan et al. |
| 6,087,493 A | 7/2000 | Wheelhouse et al. |
| 6,103,714 A | 8/2000 | Fridovich et al. |
| 6,121,278 A | 9/2000 | Jackson et al. |
| 6,245,758 B1 | 6/2001 | Stern et al. |
| 6,287,552 B1 | 9/2001 | Tournilhac et al. |
| 6,379,679 B1 | 4/2002 | Mabrouk et al. |
| 6,379,942 B1 | 4/2002 | Davis et al. |
| 6,448,239 B1 | 9/2002 | Groves et al. |
| 6,969,707 B2 | 11/2005 | Groves et al. |
| 2003/0055032 A1 | 3/2003 | Groves et al. |

FOREIGN PATENT DOCUMENTS

| | | |
|---|---|---|
| EP | 0524161 A1 | 1/1993 |
| WO | WO-9316721 A1 | 9/1993 |
| WO | WO-9531197 A1 | 11/1995 |
| WO | WO 00/75144 | * 12/2000 |
| WO | WO-0075144 A2 | 12/2000 |

OTHER PUBLICATIONS

Vippagunta et al., Adv. Drug Del. Rev. 45 (Mar. 26, 2001).*
Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*
Banker, ed. "Prodrugs." Modern Pharmaceuticals. New York: Wiley & Sons. 3(1996):596.
Batainic-Haberle et al. "New Class of Potent Catalysts of O2-Dismutation." *Dalton Trans*. (2004):1696-1702.
Batinic-Haberle et al. "The Ortho Effect Makes Manganese(III)*Meso*-Tetrakis(*N*-Methylpyridinium-2-yl-Porphyrin a Powerful and Potentially Useful Superoxide Dismutase Mimic." *J. Biol. Chem*. 273(1998):24521-24528.
Benov et al. "Isomeric *N*-alkylpyridylporphyrins and Their Zn(III) Complexes: Inactive as SOD Mimics but Powerful Photosensitizers." *Arch. Biochem. Biophys*. 402.2(2002):159-165.
Cahn et al. "An Introduction to the Sequence Rule: A System for the Specification of Absolute Configuration." *J. Chem. Educ*. 41.3(1964):116.
Cahn et al. "Specification of Molecular Chirality." *Angew. Chem. Int. Ed*. 5.4(1966):385-415. Errata 5.4(1966):511.
Cahn et al. "The Specification of Asymmetric Configuration in Organic Chemistry." *Experientia*. 12(1956):81-94.
Caminos et al. "Synthesis of Asymmetrically Meso-Substituted Porphyrins Bearing Amino Groups as Potential Cationic Photodynamic Agents." *J. Porphyrins Phthalocynanines*. 9.5(2005):334-342.
Campestrini et al. "Olefin Epoxidation and Alkane Hydroxylation Catalyzed by Robust Sulfonated Manganese and Iron Porphyrins Supported on Cationic Ion-Exchange Resins." *Inorg. Chem*. 31.11(1992):1999-2006.
Chemical Abstracts 112:146394(1990).
Chemical Abstracts 113:143962 (1990).
Chemical Abstracts 120:94146 (1992).
Chemical Abstracts 123:354281 (1995).
Chemical Abstracts 126:324503 (1997).
Chemical Abstracts 128:123775 (1997).
Chemical Abstracts 129:170516 (1998).
Crow. "Manganese and Iron Porphyrins Catalyze Peroxynitrite Decomposition and Simultanesouly Increase Nitration and Oxidant Yield: Implications for Their use as Peroxynitrite Scavengers in Vivo." *Arch. Biochem. Biophys*. 371.1(1999):41-52.
Dabrowiak et al. "Mossbauer Spectra of Iron Complexes with Macrocyclic Ligands." *J. Am. Chem. Soc*. 95.20(1973):6613-6622.
Datta et al. "Kinetic Selectivity in the N-Alkylation of 2-Pyridyl Porphyrins: a Facile Approach to the ααββ Scaffold." J. Org. Chem. 72(2007):1818-1821.

(Continued)

Primary Examiner — Paul V. Ward
(74) Attorney, Agent, or Firm — Mintz Levin Cohn Ferris Glovsky and Popeo, P.C.; Ivor R. Elrifi

(57) ABSTRACT

This invention provides a novel class of substituted macrocyclic porphyrin compounds. The compounds are useful as peroxynitrite decomposition catalysts. Pharmaceutical compositions, and methods of making and using the compounds, or a pharmaceutically acceptable salt, hydrate, or prodrug thereof are also described.

17 Claims, No Drawings

OTHER PUBLICATIONS

Ferrer-Sueta et al. "Catalytic Scavenging of Peroxynitrite by Isomeric Mn(III) N-Methylpyridylporphyrins in the Presence of Reductants." *Chem. Res. Toxicol.* 12.5(1999):442-449.
Fiel et al. "DNA Strand Scission Activity of Metalloporphyrins." *Biochem. Biophys. Res. Commun.* 107.3(1982):1067-1074.
Groves. "Artificial Enzymes: The Importance of Being Selective." *Nature.* 389(1997):329-330.
Groves. "Peroxynitrite: Reactive, Invasive and Enigmatic." *Chem. Biol.* 3(1999):226-235.
Hambright et al. "Acid-Base Equilibriums, Kinetics of Copper Ion Incorporation, and Acid-Catalyzed Zinc Ion Displacement from the Water-Soluble Porphyrin $\alpha,\beta,\gamma,\delta$-Tetrakis(4-N-methylpyridyl))porphine." *Inorg. Chem.* 9.7(1970):1757-1761.
Hartmann et al. "Synthesis of Water-Souble Ruthenium Porphyrins as DNA Cleavers and Potential Cytotoxic Agents." *JBIC.* 2(1997):427-432.
Hawker et al. "Design, Synthesis, and Properties of Dendritic Macromolecules." Step-Growth *Polymers for High-Performance Materials: New Synthetic Methods*. Washington, D.C.: Am. Chem. Soc. Hedrick, et al., ed. (1995):186-196.
Hunt et al. "Amphiphilic Peroxynitrite Decomposition Catalysts in Liposomal Assemblies." *Chem. Biol.* 4.11(1997):845-858.
Imai et al. "Chiral Recognition of Amino Acids and Dipeptides by a Water-Soluble Zinc Porphyrin." *Inorg. Chem.* 43.4(2004):1211-1213.
Ischiropoulos et al. "Peroxynitrite-Mediated Tyrosine Nitration Catalyzed by Superoxide Dismutase." *Arch. Biochem. Biophys.* 298.2(1992):431-437.
Jin et al. "Unusual Kinetic Stability of a Ground-State Singlet Oxomanganese(V) Porphyrin." *J. Am. Chem. Soc.* 121.12(1999):2923-2924.
Jori et al. "Evidence for a Major Role of Plasma Lipoproteins as Hematoporphyrin Carriers in Vivo." *Cancer Lett.* 24.3(1984):291-297.
Kachadourian et al. "High-Performance Liquid Chromatography with Spectrophotometric and Electrochemical Detection of a Series of Manganese(III) Cationic Porphyrins." *J. Chromatogr. B.* 767.1(2002):61-67.
Kim. "Highly Branched Polymers." *Polymeric Materials Encyclopedia*. New York: CRC Press. Salamone, ed. 5(1996):3049-3053.
Koppenol et al. "Syntheses of Peroxynitrite: to Go With the Flow or on Solid Grounds?" *Nitric Oxide, Part B.* 269(1996):296-302.
Lee et al. "Mechanisms of Iron Porphyrin Reactions with Peroxynitrite." *J. Am. Chem. Soc.* 120.30(1998):7493-7501.
Lee et al. "Rapid Decomposition of Peroxynitrite by Manganese Porphyrin-Antioxidant Redox Couples." *Bioorg. Med. Chem. Lett.* 7.22(1997):2913-2918.
Lindsey et al. "Investigation of the Synthesis of Ortho-Substituted Tetraphenylporphyrins." *J. Org. Chem.* 54.4(1989):828-836.
Liu et al. "Comparison of Yttrium and Indium Complexes of DOTA-BA and DOTA-MBA: Models for 90Y—and 111In-Labeled DOTA-Biomolecule Conjugates." *Bioconj. Chem.* 13.4(2002):902-913.
Malmstroem et al. "Hyperbranched Aliphatic Polyesters." *Macromol.* 28.5(1995):1698-1703.
Maraval et al. "Porphyrin-Aminoquinoline Conjugates as Telomerase Inhibitors." *Org. Biomol. Chem.* 1.6(2003):921-927.
Martin et al. "Square-Planar Nickel(II) and Copper(II) Complexes Containing 14- and 15- membered Tetraaza Macrocylic Ligands." *Inorg. Chem.* 12.7(1973):1477-1482.
Meunier et al. "Mechanism of Oxidation Reactions Catalyzed by Cytochrome P450 Enzymes." *Chem. Rev.* 104.9(2004):3947-3980.
Mikros et al. "Interactions of Water-Soluble Zinc APorphyrin with Amino Acids." *Inorg. Chim. Acta.* 153.4(188):199-200.
Misko et al. "Characterization of the Cytoprotective Action of Peroxynitrite Decomposition Catalysts." *J. Biol. Chem.* 273(1998):15646-15653.
Mizutani et al. "Molecular Recognition and Atropisomerization of [5,10,15,20-Tetrakis(1-penty1-3-pyridinio)porphyrinato]zinc(II) in Water." *Bull. Chem. Soc. Jpn.* 71.2(1990):413-418.

Pasternack et al. "Solution Properties of Tetrakis-(4-N-Methyl)Pyridylporphineiron(III)." *J. Inorg. Nucl. Chem.* 39(1977):1865-1870.
Prado-Manso et al. "Characterization and Catalytic Activity of Iron(III) mono(4-N-methyl pyridyl)-tris(halophenyl) Porphyrins in Homogeneous and Heterogeneous Systems." *J. Mol. Catal. A:Chem.* 150.1-2(1999):251-266.
Reedijk. "Medicinal Applications of Heavy-Metal Compounds." *Chem. Biol.* 3(1999):236-240.
Riley et al. "Novel Five-Coordinate Iron(III) Complexes Produced by Oxidation of Square-Planar (S=1) Iron(II) Complexes." *Inorg. Chem.* 23.20(1984):3235-3241.
Riley et al. "Synthesis and Characterization of Square-Planar Iron(II) Complexes with Dianionic Tetraaza Macrocyclic Ligands and Their Novel Derivatives." *J. Am. Chem. Soc.* 99.3(1977):767-777.
Riley et al. "The Synthesis, Structures and Properties of New Macrocyclic Ligands and Novel Sexadentate Iron Complexes Produced by Electrophilic Reactions of the Iron Derivatives." *J. Am. Chem. Soc.* 98.7(1976):1752-1762.
Robert et al. "Catalase Modeling with Metalloporphyrin Complexes Having an Oxygen Ligand in a Proximal Position." *Inorg. Chem.* 30.4(1991):706-711.
Roovers et al. "Dendrimers and Dendrimer-Polymer Hybrids." *Advances in Polymer Science*. New York: Springer. Roovers, ed. 142(1999):179-228.
Saha et al. "Determination of Optimal Conditions for Synthesis of Peroxynitrite by Mixing Acidified Hydrogen Peroxide with Nitrite." *Free Rad. Biol. Med.* 24.4(1998):653-659.
Shimanovich et al. "Mechanisms of Peroxynitrite Decomposition Catalyzed by FeTMPS, a Bioactive Sulfonated Iron Porphyrin." *Arch. Biochem. Biophys.* 387.2(2001):307-317.
Shimanovich et al. "Mn(III)-Texaphyrin as a Catalyst for the Decomposition for Peroxynitrite." *J. Am. Chem. Soc.* 123.15(2001):3613-3614.
Spasojevic et al. "Electrostatic Contribution in the Catalysis of O2 Dismutation by Superoxide Dismutase Mimics." *J. Biol. Chem.* 278(2003):6831-6837.
Szabo et al. "Part 1: Pathogenetic Role of Peroxynitite in the Development of Diabetes and Diabetic Vascular Complications: Studies with FP15, A Novel Potent Peroxynitrite Decomposition Catalyst." *Mol. Med.* 8.10(2002):571-580.
Tomalia et al. "Starburst Dendrimers: Molecular-Level Control of Size, Shape, Surface Chemistry, Topology, and Flexibility from Atoms to Macroscopic Matter." *Angew. Chem. Int. Ed. Eng.* 29.2(1990):138-175.
Uppu et al. "Selecting the Most Appropriate Synthesis of Peroxynitrite." *Meth. Enzym.* 269(1996):285-296.
Valduga et al. "Photosensitization of Wild and Mutant Strains of *Escherichia coli* by meso-Tetra (N-methyl-4-pyridyl)porphine." *Biochem. Biophys Res. Commun.* 256.1(1999):84-88.
Walker et al. "The Isocratic Separation and Indirect UV Detection of Inorganic Anions and Mono-Carboxylic and Di-Carboxylic Acids on a Low-Capacity Anion-Exchange Column." *J. Liquid Chromatogr.* 14.7(1991):1351-1366.
Watkins et al. "Iron(II) Complexes with Unsubstituted Saturated Tetraaza Macrocyclic Ligands of Varying Ring Size." *Inorg. Chem.* 15.2(1976):387-393.
Wietzerbin et al. "Hydroxylation, Epoxidation, and DNA Cleavage Reactions Mediated by the Biomimetic Mn-TMPyP/O2/Sulfite Oxidation System." *Inorg. Chem.* 38.18(1999):4123-4127.
Wolff, ed. *Burger's Medicinal Chemistry*. 5th ed., vol. 1 (1995):975-977.
Young et al. "Gadolinium(III) Texaphyrin: A Tumor Selective Radiation Sensitizer that is Detectable by MRI." *PNAS.* 93.13(1996):6610-6615.
Zipplies et al. "Influence of Hydrogen Ion Activity and General Acid-Base Catalysis on the Rate of Decomposition of Hydrogen Peroxide by a Novel Nonaggregating Water-Soluble Iron(III) Tetraphenylporphyrin Derivative." *J. Am. Chem. Soc.* 108.15(1986):4433-4445.

* cited by examiner

PORPHYRIN CATALYSTS AND METHODS OF USE THEREOF

RELATED APPLICATIONS

This is a U.S. national stage application, filed under 35 U.S.C. 371, of International Application PCT/US2007/021445, filed Oct. 5, 2007, which claims priority to U.S. provisional application Ser. No. 60/850,179, filed Oct. 6, 2006.

STATEMENT AS TO FEDERALLY SPONSORED RESEARCH

This invention was made with Government support under NIH Grant GM 36298 awarded by the National Institutes of Health. The government has certain rights in the invention.

FIELD OF THE INVENTION

The invention relates in general to substituted porphyrin compounds.

BACKGROUND OF THE INVENTION

The peroxynitrite ion (ONOO$^-$) is a potent oxidant formed by the combination of nitric oxide (NO) and the superoxide anion ($O_2$)—. NO has been shown to be generated by numerous cell types, such as macrophages, neutrophils, hepatocytes and endothelial cells. The direct combination of NO with $O_2$ produces the peroxynitrite ion (ONOO$^-$), which decomposes rapidly under physiological conditions to oxidizing intermediates. These oxidizing intermediates can damage biological targets.

Pathological consequences associated with damage to biological targets can include the oxidizing or nitrating of proteins, lipids and DNA. ONOO$^-$ crosses lipid membranes at a rate significantly faster than the rates of other known oxidants, indicating that this oxidant can travel distances of cellular dimensions. Thus, even in the presence of biological membranes, ONOO$^-$ can have free access to cellular interiors. ONOO$^-$ is also known to nitrate tyrosine residues in proteins, and to oxidize sulfhydryls, methionines and macromolecules such as, for example, metalloenzymes, DNA, and lipids.

In light of this reactivity, ONOO$^-$ has been implicated in a variety of diseases. These diseases include, e.g., neurodegenerative disorders such as Alzheimer's disease, amyotrophic lateral sclerosis, stroke, AIDS dementia and Huntington's disease; heart diseases such as atherosclerosis; chronic inflammation and autoimmune diseases such as arthritis, inflammatory bowel disease, and acute respiratory disease syndrome; cancer; ischemia-reperfusion injury; septic shock; and chronic rejection of renal grafts.

SUMMARY OF THE INVENTION

The invention is based in part on the discovery of substituted 2-pyridyl porphyrin compounds that are effective peroxynitrite decomposition catalysts. 2-pyridyl porphyrin compounds have one or more of the properties of high catalytic activity, high stability and enhanced lifetime in the blood pool, advantageous tissue distribution, and low toxicity. The peroxynitrite decomposition catalysts can be used to treat a variety of conditions and diseases, including those known to result from the accumulation of peroxynitrite.

Accordingly, in one aspect the invention provides a compound having the Formula I:

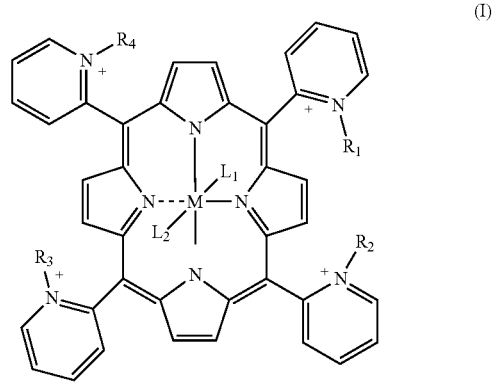

(I)

or a pharmaceutically acceptable base or acid addition salt, hydrate, ester, solvate, prodrug, metabolite, or stereoisomer, or mixtures thereof. In one embodiment, at least one of $R_1$, $R_2$, $R_3$, and $R_4$ is independently selected from the group consisting of $CH_2C(O)NR_5R_6$ and $(CH_2CH_2O)_tCH_3$ and the remaining $R_1$, $R_2$, $R_3$, and $R_4$ are hydrogen. t is selected from 1, 2, 4, 5, 6, 7, 8, 9, and 10.

$R_5$ and $R_6$ are selected from the group consisting of H, $CH_2CH_2OCH_3$, $CH_2CH_2OCH_2CH_2OCH_3$, $CH_2CH_2OCH_2CH_2OCH_2CH_2OCH_3$, $CH_2COO$, $(CH_2)_n$—X, $(CH_2)_n$—Y, $(CH_2)_nR_9$—X, $(CH_2)_nR_9$—Y, $CH_2CO_2CH_2CH_3$, $(OCH_2CH_2)_m$—X, $(OCH_2CH_2)_m$—Y, $Y_2$—X, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)$—$Y_2$—$C(Zs)_3$, wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O$; $(CH_2)_nOCH_2C(CH_2OH)_3$, $(CH_2)_nOCH_2CH(CH_2OH)_2$, $(CH_2)_nOCH_2C(CH_2OH)_2$ $(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH$—Y, $CH_2CO$—Y, $CH_2CO(CH_2)_p$—Y; alkyl, cycloalkyl, and aralkyl.

n is an integer selected from 1, 2, 3, 4, 5, 6, 7, 8, 9, and 10. m is an integer from 1 to 200. p is 1 or 2. X is COOH, COOR', $CONH_2$, CONHR', $CONR'_2$, $CO(CH_2)_pR'$, $OPO_3H_2$, $PO_3H_2$, $SO_3H$, $NH_2$, $NR_2$, or $NR'_3^+$, a steroid, an amino acid, an oligosaccharide, a peptide, or a polycarboxylic acid. R' is alkyl $CH_2CH_2OCH_3$, $CH_2CH_2OCH_2CH_2OCH_3$, $(CH_2)_n$—X, $(CH_2)_n$—Y, $(CH_2)_nAr$—X, $(CH_2)_nAr$—Y, $CH_2CH_2OCH_2CH_2OCH_2CH_2OCH_3$, $CH_2CO_2CH_2CH_3$, $(OCH_2CH_2)_m$—X, $(OCH_2CH_2)_m$—Y, $Y_2$—X, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)$—$Y_2$—$C(Zs)_3$, wherein: Zs is $CH_2OCH_2CH_2C(O)Y_2C(Z_6)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2$ $(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CCH_2OX)_3]_3$, $CH_2CONH$—Y, $CH_2CO$—Y, and $CH_2CO(CH_2)_p$—Y;

Y is OH or $(OCH_2CH_2)_m$—$W_1$ or $(CH_2CH_2)_m$—$W_2$; where $W_1$ is OH, or $(OCH_2CH_2)_mOH$ and $W_2$ is OR". R" is an alkyl group. $Y_2$ is selected from the group consisting of $(CH_2)_nO$, $(CH_2)_nNH$, and $(CH_2)_nS$, $CH_2CONH$, $CH_2COO$, or $CH_2CO(CH_2)_p$.

$R_9$ is substituted phenyl, unsubstituted phenyl, substituted napthyl, or unsubstituted napthyl. $L_1$ and $L_2$ are, independently, absent, halide, oxo, $OH_2$, hydroxo, CN, $OPO_3H$ or alcohol; and M is absent, Mn or Fe. In one embodiment, $R_5$ and $R_6$ are not both alkyl.

In one embodiment, at least one of $R_1$, $R_2$, $R_3$, or $R_4$ is $CH_2C(O)NR_5R_6$. In another embodiment, at least two of $R_1$, $R_2$, $R_3$, or $R_4$ $CH_2C(O)NR_5R_6$ in another embodiment, at least three of $R_1$, $R_2$, $R_3$, or $R_4$ are $CH_2C(O)NR_5R_6$. In another embodiment, $R_1$, $R_2$, $R_3$, and $R_4$ are each $CH_2C(O)NR_5R_6$.

In one embodiment, M is Mn or Fe. In another embodiment, M is absent.

In one embodiment, one of $R_5$ or $R_6$ is H. In another embodiment, one of $R_5$ or $R_6$ is selected from aralkyl, alkyl, cycloalkyl, substituted cycloalkyl, and $CH_2CH_2OCH_3$. In one embodiment, one of $R_5$ or $R_6$ is aralkyl.

In another embodiment, aralkyl is $(CR_7R_8)_s$—$R_9$. In one embodiment, $R_7$ and $R_8$ are, independently, selected from H, alkyl, OH, and halogen. In another embodiment, s is 1, 2, 3, 4, 5, 6, 7, 8, 9, or 10. In one embodiment, one of $R_7$ or $R_8$ is H. In another embodiment, one of $R_7$ or $R_8$ is alkyl. In one embodiment, $R_9$ is phenyl. In another embodiment, s is 1. In one embodiment, aralkyl is

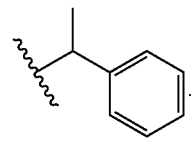

In another embodiment, aralkyl is

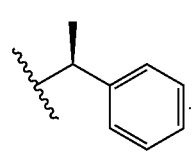

In another embodiment, aralkyl is

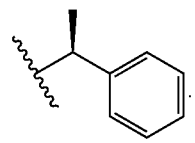

In one embodiment, one of $R_5$ or $R_6$ is selected from alkyl, cycloalkyl, or substituted cycloalkyl. In another embodiment, cycloalkyl or substituted cycloalkyl is a bicyclic or tricyclic ring system. In one embodiment, the bicyclic ring system is bicycle[2.2.1]heptane. In another embodiment, the bicyclic ring system is 1,7,7-trimethylbicyclo[2.2.1]heptane. In one embodiment, one of $R_5$ or $R_6$ is $CH_2CH_2OCH_3$.

In one embodiment, at least one of $R_1$, $R_2$, $R_3$, or $R_4$ is $(CH_2CH_2O)_tCH_3$. In another embodiment, at least two of $R_1$, $R_2$, $R_3$, or $R_4$ are $(CH_2CH_2O)_tCH_3$. In another embodiment, at least three of $R_1$, $R_2$, $R_3$, or $R_4$ are $(CH_2CH_2O)_tCH_3$. In another embodiment, $R_1$, $R_2$, $R_3$, and $R_4$ are $(CH_2CH_2O)_tCH_3$. In one embodiment, t is 1.

In one embodiment, the compound is a mixture of atropoisomers αααα, αααβ, ααββ, and αβαβ. In another embodiment, the compound is an ααββ atropisomer. In one embodiment, the compound is selected from

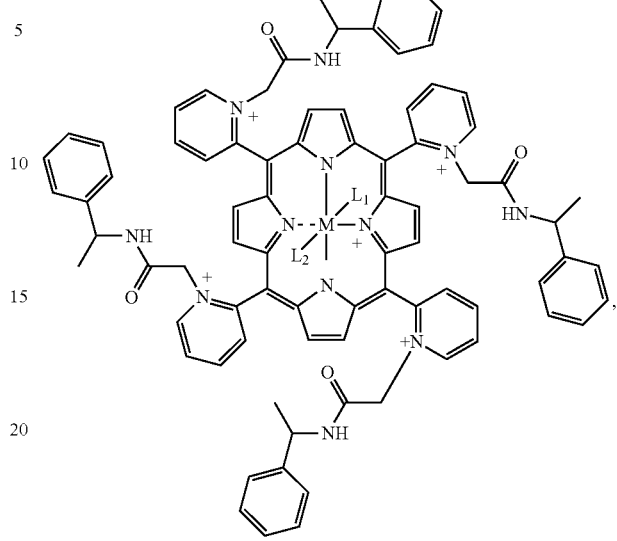

1

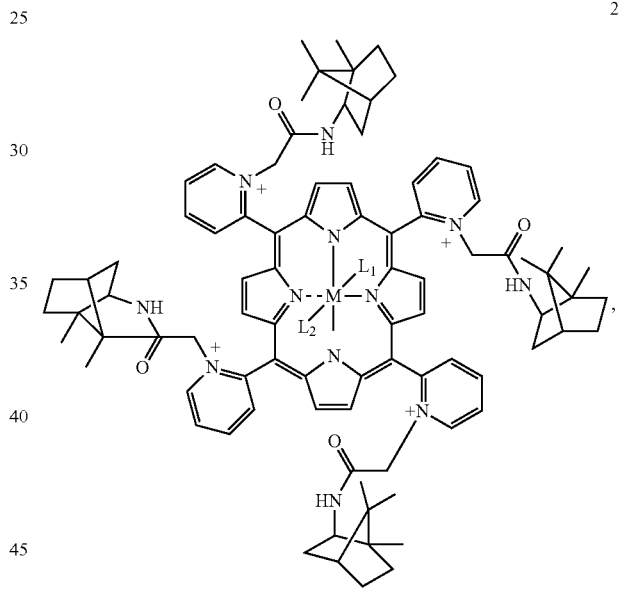

2

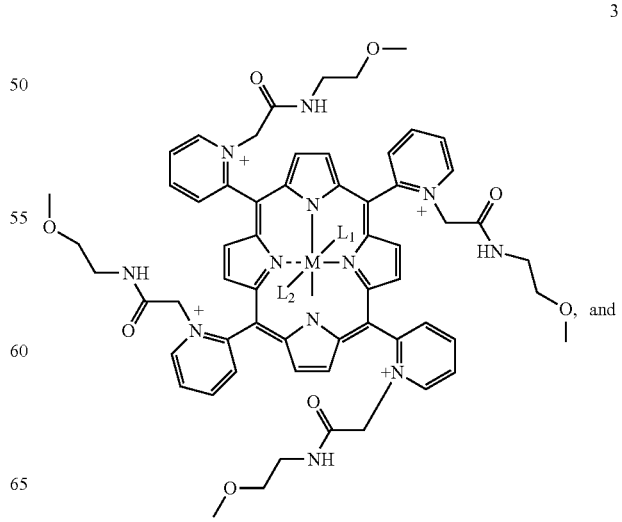

3

-continued

4

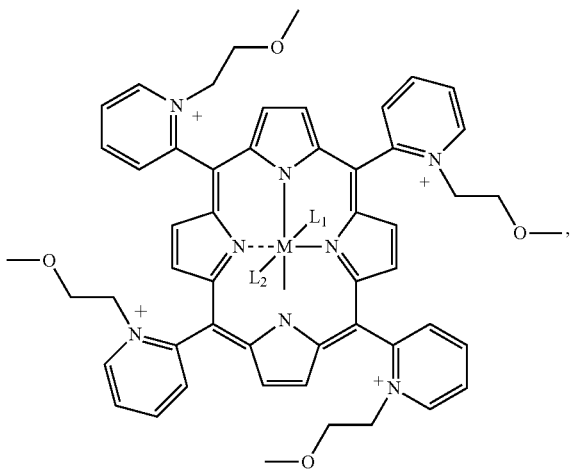

wherein L and L$_2$ are, independently, absent, halide, oxo, OH$_2$, hydroxo, CN, OPO$_3$H or alcohol; and M is absent, Mn or Fe.

One aspect of the invention includes a pharmaceutical composition comprising the compound of formula I and a pharmaceutically acceptable carrier. Another embodiment of the invention includes a method of lowering peroxynitrite levels in a cell or tissue, the method comprising contacting said cell or tissue with a compound of formula I in an amount sufficient to lower peroxynitrite levels in said cell or tissue. Another embodiment includes a method of treating or inhibiting the development of a pathology associated with peroxynitrite damage in a subject, the method comprising administering to a subject in need thereof a therapeutically effective amount of the compound of formula I. In another embodiment, the pathology is selected from the group consisting of Alzheimer's disease, amyotrophic lateral sclerosis, stroke, AIDS dementia, Huntington's disease, atherosclerosis, inflammation, arthritis, neurodegeneration, sepsis, autoimmune diseases, cancer, ischemia-reperfusion injury, septic shock, diabetes, diabetic vascular complications, diabetic cardiomyopathy, diabetic neuropathy, hyperglycemia, pathophysiological conditions of the heart, acute myocardial infarction, chronic ischemic heart failure, doxorubicin-induced cardiac disfunction, oxidative stress, obliterative bronchiolitis, colitis, vascular dysfunction, myocardial dysfunction, myocardial necrosis, and chronic graft. In another embodiment, the subject is a human.

The details of one or more embodiments of the invention are set forth in the accompanying description below. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

DETAILED DESCRIPTION OF THE INVENTION

The invention provides novel substituted macrocyclic compounds that can be complexed to a metal to form metallic compounds. The compounds are useful as e.g., peroxynitrite decomposition catalysts. The compounds include porphyrin complexes containing substituted 2-pyridine substituents.

The invention is based in part on the discovery that substituted 2-pyridyl porphyrins are unexpectedly effective peroxynitrite decomposition catalysts. Substituents on compounds as described herein can result in increased biocompatibility, which can be characterized as producing at least one of the following effects: (1) enhancement of the ONOO$^-$ decomposition activity of the complex; (2) enhanced stability and half-life in vivo; (3) optimized tissue distribution throughout the body; and (4) lowered toxicity when administered to a subject. In some embodiments, the substituted compounds are present in liposomes.

Porphyrin compounds have a wide range of applications as water-soluble oxidation catalysts (Meunier, B. *Chem. Rev.* 2004, 104, 3947-3980; Jin, N. *J. Am. Chem. Soc.* 1999, 121, 2923-2924; Wietzerbin, K. *Inorg. Chem.* 1999, 38, 4123-4127; Prado-Manso, C. *J. Mol. Catal. A: Chem.* 1999, 150, 251-266) and as hosts for the molecular recognition of small molecules in water (Imai, H. *Inorg. Chem.* 2004, 43, 1211-1213, Mizutani, T. *Bull. Chem. Soc. Jpn.* 1998, 71, 413-418, Mikros, F. *Inorg. Chim. Acta* 1988, 153, 199-200). Further, some porphyrins have shown considerable promise as therapeutic agents such as superoxide dismutase mimics (Batainic-Haberle, I. *J. Chem. Soc., Dalton Trans.* 2004, 1696-1702; Spasojevic, I. *J. Biol. Chem.* 2003, 278, 6831-6837; Kachadourian, R. *J. Chromatogr. B* 2002, 767, 61-67), photosensitizers (Caminos, D. A. *J. Porphyrins Phthalocyanines* 2005, 9, 334-342; Benov, L. *Arch. Biochem. Biophys.* 2002, 402, 159-165; Pandey, R. In *The Porphyrin Handbook*; Kadish, K., Smith, K., Guilard, R., Eds.; Academic Press: 2000; Vol. 6, p 157-230; Valduga, G. *Biochem. and Biophys. Res. Commun.* 1999, 256, 84-88; Jori, G. *Cancer Lett.* 1984, 24, 291-297), DNA cleavers (Maraval, A. *Org. Biomol. Chem.* 2003, 1, 921-927; Hartmann, M. *J. Biol. Inorg. Chem.* 1997, 427-432, Fiel, R. *J. Biochem. Biophys. Res. Commun.* 1982, 107, 1067-1074) and peroxynitrite decomposition catalysts (Szabo, C. *Mol. Med.* 2002, 8, 571-580; Shimanovich, R. *J. Am. Chem. Soc.* 2001, 123, 3613-3614; Fridovich, I. *Chem. Res. Toxicol.* 1999, 12, 442-449; Crow, J. P. *Arch. Biochem. Biophys.* 1999, 371, 41-52; Groves, J. *J. Am. Chem. Soc.* 1998, 120, 7493-7501). Alkylation of the pyridyl nitrogen of meso-(pyridyl)-porphyrins (Hambrigh, P. *Inorg. Chem.* 1970, 9, 1757-1761) is one attractive synthetic strategy to generate cationic porphyrins. Metallated meso-tetrakis-(N-alkylpyridinium-2-yl)-porphyrins are of particular interest since they have been shown to have superior superoxide dismutase (Fridovich, I. *J. Biol. Chem* 1998, 273, 24521-24528) and peroxynitrite decomposition properties (Szabo, C. *Mol. Med.* 2002, 8, 571-580) relative to the 3-pyridyl and 4-pyridyl isomers and high potency in animal models of inflammatory disease. The 2-pyridyl isomers also offer potential synthetic access to chiral metalloporphyrin scaffolds for use as water-soluble oxidation catalysts and hosts for chiral recognition.

Structures of Macrocyclic Compounds and Metal Complexes

Compounds of the invention include substituted 2-pyridyl porphyrins, where the metal and ligands are absent. Compounds of the invention also include metal complexes. The invention also includes equivalents of the general formula set forth above for the compounds, as well as the intermediates of the compounds that have the same general properties as these compounds. Also included are analogs of the compounds, e.g., compounds wherein one or more of the various R$_1$, R$_2$, $R_3$, and $R_4$ groups are simple variations of the substituents as defined therein, or substituents which are a higher alkyl group than that indicated.

Accordingly, one aspect the invention provides a novel substituted porphyrin compound falling within formula I:

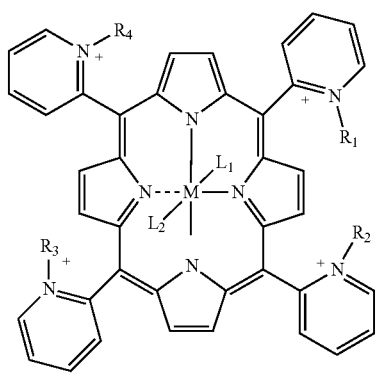

(I)

$R_1$, $R_2$, $R_3$, and $R_4$ are selected from $CH_2C(O)NR_5R_6$ and $(CH_2CH_2O)_tCH_3$, wherein t is 1, 2, 4, 5, 6, 7, 8, 9, or 10, and the remaining $R_1$, $R_2$, $R_3$, and $R_4$ are hydrogen. $R_5$ and $R_6$ include, independently, H, alkyl, cycloalkyl, aralkyl, one or more linear, dendritic or branched polyethers, such as polyalkylene glycols (e.g., polyethylene glycol (PEG) moieties), linear, dendritic or branched polycarboxylic acids, amides, phosphates, phosphonic acids, sulfonic acids, amines, steroids, amino acids, oligosaccharides, or peptides.

A "dendritic polymer" is a polymer exhibiting regular dendritic branching i.e. branching like a tree. It can be formed by the sequential or generational addition of branched layers to or from a core. The term dendritic polymer encompasses "dendrimers", which include a core, at least one interior branched layer, and a surface branched layer (see, e.g., Petar et al., Pages 641-645 in: Chem. in Britain, (August 1994). A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron.

Highly branched dendritic polymers are well known and are discussed in, e.g., "Polymeric Materials Encyclopedia," Vol. 5 (1996), J. C. Salamone, Ed., CRC Press, New York, pp. 3049-3053. Dendritic polymers have a non-linear architecture and are intrinsically globular in shape. Discrete, stepwise synthetic methods are used to prepare highly branched pure compounds, or dendrimers. As discussed by Hawker and Devonport in "Step-Growth Polymers for High-Performance Materials: New Synthetic Methods," Hedrick, J. L. and Labadie, J. W., Eds., Am. Chem. Soc., Washington, D.C., 1996, pp. 186-196, if the macromolecule has highly regular branching which follows a strict geometric pattern, it is a dendrimer. Dendrimers are typically monodisperse and are prepared in a multi-step approach with purifications at each stage.

The architecture of dendrimers is also discussed by Roovers and Comanita in "Advances in Polymer Science," Vol. 142 (1999), Roovers, J., Ed., Springer, New York, pp. 179-228. Dendrimers consist of a core molecule which defines the center of symmetry of the molecule, and branching layers. Tomalia, et al., in Angew. Chem. Int. Ed. Eng., 29 (1990), 138-175 disclose "starburst" dendrimers which consist of an initiator core and branching groups.

Dendritic polymers include, but are not limited to, symmetrical and unsymmetrical branching dendrimers, cascade molecules, arborols (dumbbell shaped molecules in which a hydrophobic spacer separates two hydrophilic end groups), dense star polymers (symmetric, with branch arms of equal length, as disclosed in U.S. Pat. No. 5,714,166), and the like.

In some embodiments, the compounds are hyperbranched. Hyperbranched compounds result if the branching is random and irregular and are therefore not monodisperse. As discussed by Malmstroem, et al., in Macromolecules, 28 (1995), 1698-1703, a hyperbranched material contains a mixture of linear and fully branched repeating units and has a degree of branching of less than unity. A preferred dendritic substance has a degree of branching of unity. Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Peptidic dendrimer- and branched-peptides are disclosed in, e.g., U.S. Pat. Nos. 6,379,679, 5,714,166 and 5,622,933. Branched and hyperbranched polyetherimides are disclosed in, e.g., U.S. Pat. No. 6,287,552. Enzymes modified by dendrimers are disclosed in, e.g., U.S. Pat. No. 6,379,942.

One aspect of the invention includes a compound having the Formula I:

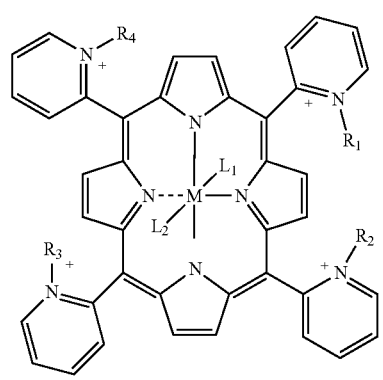

(I)

or a pharmaceutically acceptable base or acid addition salt, hydrate, ester, solvate, prodrug, metabolite, or stereoisomer, or mixtures thereof. In one embodiment, at least one of $R_1$, $R_2$, $R_3$, and $R_4$ is independently selected from the group consisting of $CH_2C(O)NR_5R_6$ and $(CH_2CH_2O)_tCH_3$ and the remaining $R_1$, $R_2$, $R_3$, and $R_4$ are hydrogen. t is 1, 2, 4, 5, 6, 7, 8, 9, or 10. $R_5$ and $R_6$ are selected from H, $CH_2CH_2OCH_3$, $CH_2CH_2OCH_2CH_2$ $OCH_3$, $CH_2CH_2OCH_2CH_2OCH_2CH_2OCH_3$, $CH_2COO$, $(CH_2)_n$—X, $(CH_2)_n$—Y, $(CH_2)_nR_9$—X, $(CH_2)_nR_9$—Y, $CH_2CO_2CH_2CH_3$, $(OCH_2CH_2)_m$—X, $(OCH_2CH_2)_m$—Y, $Y_2$—X, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)$—$Y_2$—$C(Zs)_3$, wherein: Zs is $CH_2OCH_2CH_2C(O)Y_2C(Z_6)_3$ and $Z_6$ is $CH_2OCH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2$ $(CH_3)$, $(CH_2)OCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH$—Y, $CH_2CO$—Y, $CH_2CO(CH_2)_p$—Y; alkyl, cycloalkyl, and aralkyl. n is an integer selected from 1, 2, 3, 4, 5, 6, 7, 8, 9, and 10. m is an integer from 1 to 200. p is 1 or 2. X is COOH, COOR', CONH$_2$, CONHR', CONR'$_2$, CO(CH$_2$)$_p$R', OPO$_3$H$_2$, PO$_3$H$_2$, SO$_3$H, NH$_2$, NR'$_2$, or NR'$_3^+$, a steroid, an amino acid, an oligosaccharide, a peptide, or a polycarboxylic acid. R' is alkyl, CH$_2$CH$_2$OCH$_3$, CH$_2$CH$_2$OCH$_2$CH$_2$OCH$_3$, (CH$_2$)$_n$—X, (CH$_2$)$_n$—Y, (CH$_2$)$_n$Ar—X, (CH$_2$)$_n$Ar—Y, CH$_2$CH$_2$OCH$_2$CH$_2$OCH$_2$CH$_2$OCH$_3$, CH$_2$CO$_2$CH$_2$CH$_3$, (OCH$_2$CH$_2$)$_m$—X, (OCH$_2$CH$_2$)$_m$—Y, Y$_2$—X, Y$_2$C(Z$_1$)$_3$, further wherein: Z$_1$ is CH$_2$OCH$_2$(CH$_2$)$_n$X or CH$_2$OCH$_2$(CH$_2$)Y; (CH$_2$)$_n$C(O)Y$_2$C(Z$_2$)$_3$, wherein: Z$_2$ is CH$_2$OCH$_2$CH$_2$C(C)) Y$_2$C(Z$_4$)$_3$ and Z$_4$ is CH$_2$OCH$_2$CH$_2$X; (CH$_2$)$_n$C(O)—Y$_2$—C (Z$_5$)$_3$, wherein: Z$_5$ is CH$_2$OCH$_2$CH$_2$C(O)Y$_2$C(Z$_6$)$_3$ and Z$_6$ is CH$_2$OCH$_2$CH$_2$C(O)O(CH$_2$CH$_2$O)$_m$CH$_2$CH$_2$O$^-$; (CH$_2$)$_n$ OCH$_2$C(CH$_2$OH)$_3$, (CH$_2$)$_n$OCH$_2$CH(CH$_2$OH)$_2$, (CH$_2$)$_n$ OCH$_2$C(CH$_2$OH)$_2$ (CH$_3$), (CH$_2$)$_n$OCH$_2$C[CH$_2$OCH$_2$C (CH$_2$OH)$_3$]$_3$, (CH$_2$)$_n$OCH$_2$C[CH$_2$OCH$_2$C(CH$_2$O [CH$_2$CH$_2$O]$_m$CH$_2$CH$_2$OX)$_3$]$_3$, CH$_2$CONH—Y, CH$_2$CO—Y, and CH$_2$CO(CH$_2$)$_p$—Y.

Y is OH or (OCH$_2$CH$_2$)$_m$—W$_1$ or (CH$_2$CH$_2$)$_m$—W$_2$; where W$_1$ is OH, or (OCH$_2$CH$_2$)$_m$OH and W$_2$ is OR". R" is an alkyl group. Y$_2$ is selected from the group consisting of (CH$_2$)$_n$O, (CH$_2$)$_n$NH, and (CH$_2$)S, CH$_2$CONH, CH$_2$COO, or CH$_2$CO(CH$_2$)$_p$. R$_9$ is substituted phenyl, unsubstituted phenyl, substituted napthyl, or unsubstituted naphthyl. L$_1$ and L$_2$ are, independently, absent, halide, oxo, OH$_2$, hydroxo, CN, OPO$_3$H or alcohol; and M is absent, Mn or Fe. In one embodiment, R$_5$ and R$_6$ are not both alkyl.

In one embodiment, at least one of R$_1$, R$_2$, R$_3$, or R$_4$ is CH$_2$C(O)NR$_5$R$_6$. In another embodiment, at least two of R$_1$, R$_2$, R$_3$, or R$_4$ CH$_2$C(O)NR$_5$R$_6$. In another embodiment, at least three of R$_1$, R$_2$, R$_3$, or R$_4$ are CH$_2$C(O)NR$_5$R$_6$. In another embodiment, R$_1$, R$_2$, R$_3$, and R$_4$ are each CH$_2$C(O) NR$_5$R$_6$.

In one embodiment, at least one of R$_1$, R$_2$, R$_3$, or R$_4$ is CH$_2$C(O)NR$_5$R$_6$ and the remaining R$_1$, R$_2$, R$_3$, and R$_4$ are H. In another embodiment, at least two of R$_1$, R$_2$, R$_3$, or R$_4$ CH$_2$C(O)NR$_5$R$_6$ and the remaining R$_1$, R$_2$, R$_3$, and R$_4$ are H. In another embodiment, at least three of R$_1$, R$_2$, R$_3$, or R$_4$ are CH$_2$C(O)NR$_5$R$_6$ and the remaining R$_1$, R$_2$, R$_3$, and R$_4$ are H In one embodiment, M is a metal. In another embodiment, M is tin, silicon, germanium, copper, iron, cobalt, zinc, nickel, or manganese. In one embodiment, M is Mn, Fe, or Zn. In another embodiment, M is Mn or Fe. In another embodiment, M is Mn. In another embodiment, M is Fe. In another embodiment, M is Zn. In another embodiment, M is absent.

In one embodiment, one of R$_5$ or R$_6$ is H. In one embodiment, one of R$_5$ or R$_6$ is selected from aralkyl, alkyl, cycloalkyl, substituted cycloalkyl, and CH$_2$CH$_2$OCH$_3$. In one embodiment, one of R$_5$ or R$_6$ is selected from aralkyl, alkyl, cycloalkyl, substituted cycloalkyl, and CH$_2$CH$_2$OCH$_3$ and the remaining R$_5$ or R$_6$ is H.

In one embodiment, one of R$_5$ or R$_6$ is aralkyl. In one embodiment, one of R$_5$ or R$_6$ is aralkyl and the other is H. In another embodiment, aralkyl is (CR$_7$R$_8$)$_5$—R$_9$, wherein R$_7$ and R$_8$ are, independently, selected from H, alkyl, OH, and halogen, and s is 1, 2, 3, 4, 5, 6, 7, 8, 9, or 10. In one embodiment, one of R$_7$ or R$_8$ is H. In another embodiment, one of R$_7$ or R$_8$ is alkyl. In one embodiment, one of R$_7$ or R$_8$ is methyl. In one embodiment, one of R$_7$ or R$_8$ is H and the other one of R$_7$ or R$_8$ is alkyl. In one embodiment, s is 1. In another embodiment, s is 2. In another embodiment, s is 3. In another embodiment, s is 4. In another embodiment, s is 5. In one embodiment, R$_9$ is phenyl. In another embodiment, R$_9$ is substituted phenyl. In one embodiment, aralkyl is racemic

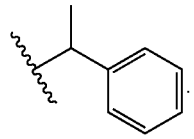

In another embodiment, aralkyl is

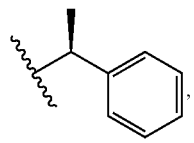

where the chiral center is in the R configuration. In another embodiment, aralkyl is

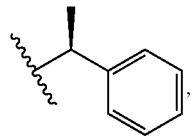

where the chiral center is in the S configuration.

In one embodiment, one of R$_5$ or R$_6$ is selected from alkyl, cycloalkyl, or substituted cycloalkyl. In another embodiment, one of R$_5$ or R$_6$ is selected from alkyl, cycloalkyl, or substituted cycloalkyl and the remaining R$_5$ or R$_6$ is H. In one embodiment, cycloalkyl or substituted cycloalkyl is a bicyclic ring system. In another embodiment, the bicyclic ring system is bicycle[2.2.1]heptane. In another embodiment, the bicyclic ring system is 1,7,7-trimethylbicyclo[2.2.1]heptane.

In one embodiment, one of R$_5$ or R$_6$ is a linear, dendritic, or branched polyether e.g., a polyethylene glycol (PEG) moiety). In another embodiment, one of R$_5$ or R$_6$ is a linear, dendritic, or branched polyether e.g., a polyethylene glycol (PEG) moiety) and the other R$_5$ or R$_6$ is H. In one embodiment, one of R$_5$ or R$_6$ is CH$_2$CH$_2$OCH$_3$. In another embodiment, one of R$_5$ or R$_6$ is CH$_2$CH$_2$OCH$_2$CH$_2$OCH$_3$. In another embodiment, one of R$_5$ or R$_6$ is CH$_2$CH$_2$OCH$_2$CH$_2$OCH$_2$CH$_2$OCH$_3$.

In one embodiment, at least one of R$_1$, R$_2$, R$_3$, or R$_4$ is (CH$_2$CH$_2$O)$_t$CH$_3$. In another embodiment, at least two of R$_1$, R$_2$, R$_3$, or R$_4$ are (CH$_2$CH$_2$O)$_t$CH$_3$. In another embodiment, at least three of R$_1$, R$_2$, R$_3$, or R$_4$ are (CH$_2$CH$_2$O)$_t$CH$_3$. In another embodiment, R$_1$, R$_2$, R$_3$, and R$_4$ are (CH$_2$CH$_2$O)$_t$CH$_3$.

In one embodiment, at least one of R$_1$, R$_2$, R$_3$, or R$_4$ is (CH$_2$CH$_2$O)$_t$CH$_3$ and the remaining R$_1$, R$_2$, R$_3$, and R$_4$ is H. In another embodiment, at least two of R$_1$, R$_2$, R$_3$, or R$_4$ are (CH$_2$CH$_2$O)$_t$CH$_3$ and the remaining R$_1$, R$_2$, R$_3$, and R$_4$ is H. In another embodiment, at least three of R$_1$, R$_2$, R$_3$, or R$_4$ are (CH$_2$CH$_2$O)$_t$CH$_3$ and the remaining R$_1$, R$_2$, R$_3$, and R$_4$ is H.

In one embodiment, t is 1. In another embodiment, t is 2. In another embodiment, t is 4. In another embodiment, t is 5. In another embodiment, t is 6. In another embodiment, t is 7. In another embodiment, t is 8. In another embodiment, t is 9. In another embodiment, t is 10.

In one embodiment, the compound is a mixture of atropoisomers αααα, αααβ, ααββ, and αβαβ. In another embodiment, the compound is an ααββ atropisomer.

In another embodiment, the compound is selected from

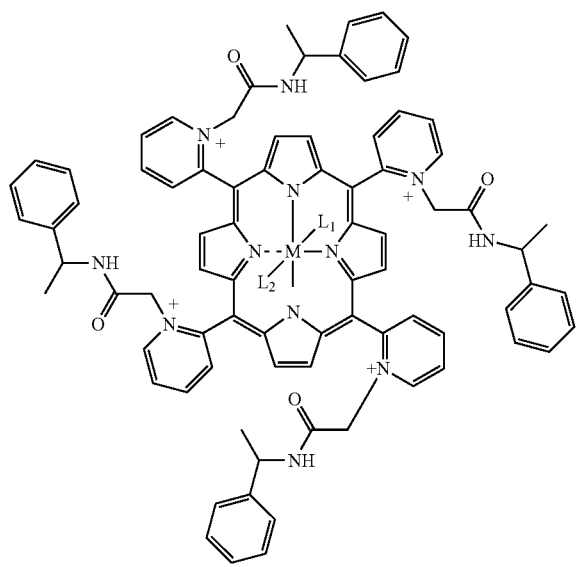

1

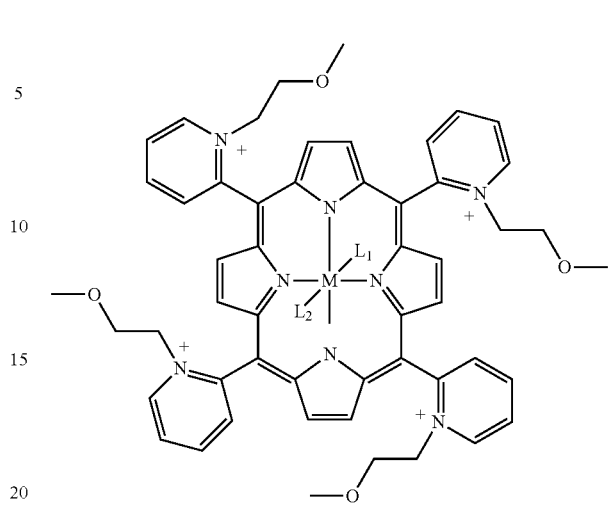

4 wherein $L_1$ and $L_2$ are, independently, absent, halide, oxo, $OH_2$, hydroxo, CN, $OPO_3H$ or alcohol; and M is absent, Mn or Fe.

One aspect of the invention includes a pharmaceutical composition comprising the compound of formula I and a pharmaceutically acceptable carrier.

Another aspect of the invention includes a method of lowering peroxynitrite levels in a cell or tissue, the method comprising contacting said cell or tissue with a compound of formula I in an amount sufficient to lower peroxynitrite levels in said cell or tissue. In one embodiment, at least one of $R_1$, $R_2$, $R_3$, or $R_4$ is $CH_2C(O)NR_5R_6$. In another embodiment, at least two of $R_1$, $R_2$, $R_3$, or $R_4$ are $CH_2C(O)NR_5R_6$. In another embodiment, at least three of $R_1$, $R_2$, $R_3$, or $R_4$ are $CH_2C(O)NR_5R_6$. In another embodiment, $R_1$, $R_2$, $R_3$, and $R_4$ are $CH_2C(O)NR_5R_6$. In another embodiment, at least one of $R_1$, $R_2$, $R_3$, or $R_4$ is $(CH_2CH_2O)_tCH_3$. In another embodiment, at least two of $R_1$, $R_2$, $R_3$, or $R_4$ are $(CH_2CH_2O)_tCH_3$. In another embodiment, at least three of $R_1$, $R_2$, $R_3$, or $R_4$ are $(CH_2CH_2O)_tCH_3$. In another embodiment, $R_1$, $R_2$, $R_3$, and $R_4$ are $(CH_2CH_2O)_tCH_3$.

Another aspect of the invention includes a method of treating or inhibiting the development of a pathology associated with peroxynitrite damage in a subject, the method comprising administering to a subject in need thereof a therapeutically effective amount of the compound of Formula I. In one embodiment, the pathology is selected from the group consisting of Alzheimer's disease, amyotrophic lateral sclerosis, stroke, AIDS dementia, Huntington's disease, atherosclerosis, inflammation, arthritis, neurodegeneration, sepsis, autoimmune diseases, cancer, ischemia-reperfusion injury, septic shock, diabetes, diabetic vascular complications, diabetic cardiomyopathy, diabetic neuropathy, hyperglycemia, pathophysiological conditions of the heart, acute myocardial infarction, chronic ischemic heart failure, doxorubicin-induced cardiac disfunction, oxidative stress, obliterative bronchiolitis, colitis, vascular dysfunction, myocardial dysfunction, myocardial necrosis, and chronic graft. In another embodiment, the subject is a human.

In one embodiment, the compounds are provided in association with suitable ligands ($L_1$ and $L_2$) and/or charge neutralizing anions. $L_1$ and $L_2$ can be the same or different, and one or more may be absent. Ligands and charge neutralizing anions can be derived from any monodentate or polydentate coordinating ligand or ligand system or the corresponding

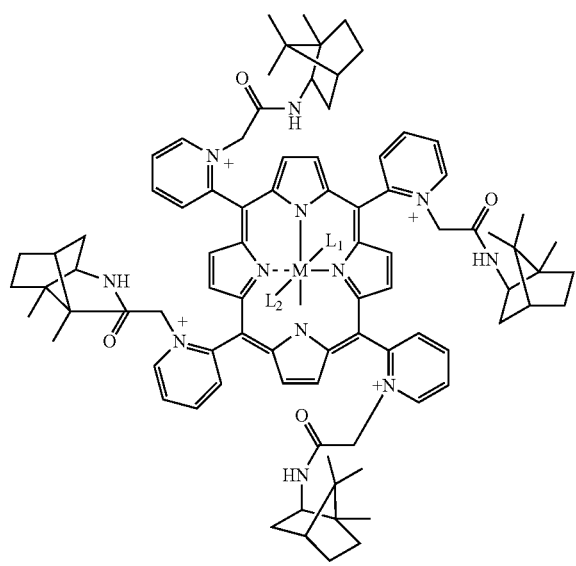

2

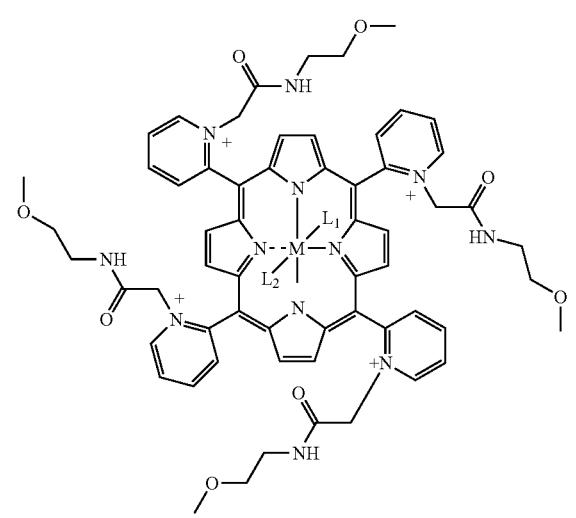

3 anion thereof. They are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl, amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isozutrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkyl aryl thiocarbamate, alkyl ditbiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroanitmonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems; with the proviso that when the charge neutralizing complex has a net positive charge, then D is a negatively charged counter ion or when the charge neutralizing complex has net negative charge then D is a counter ion selected from a group consisting of alkaline and alkaline earth cations, organic cations such as alkyl or alkylaryl ammonium cations.

Preferred ligands include halide, oxo, aquo, hydroxo and alcohol. Preferred anionic counterions include halide ions. Halide ions include fluoro, chloro, bromo or iodo ions. Ligands and counterions may be the same or different. For example, a metallic complex may have one or two chloro axial ligands and 1, 2, 3, or 4 chloride ions as charge neutralizing anions.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. Lower alkyl refers to a straight-chain or branched-chain alkyl radical containing 1, 2, 3, 4, 5, or 6 carbon atoms.

The term "cycloalkyl", alone or in combination means a cycloalkyl group containing 3 4, 5, 6, 7, 8, 9, or 10 atoms. In one embodiment, cycloalkyl contains 3, 4, 5, 6, 7, or 8 atoms, and in another embodiment, cycloalkyl contains 3, 4, 5, or 6 atoms. Examples of such cycloalkyl groups include, but are not limited to, cyclopropyl, cyclobutyl, cyclopentyl, cyclohexyl, cycloheptyl, cyclooctyl, and perhydronaphthyl.

The term "cycloalkenyl", alone or in combination, means a cycloalkyl group having one or more double bonds. Examples include, but are not limited to, cyclopentenyl, cyclohexenyl, cyclooctenyl, cyclopentadienyl, and cyclooctadienyl.

The terms cycloalkyl and cycloalkenyl include "bicyclic ring systems" which means polycyclic ring systems where rings share adjacent carbons and the rings are said to be fused or annelated. Bicyclic ring systems are characterized by two carbon atoms, the bridgehead carbons, being shared by two rings.

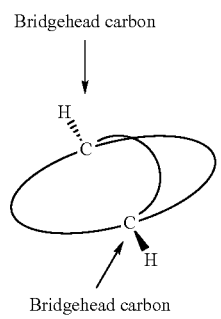

Examples of bicyclic ring systems include for example,

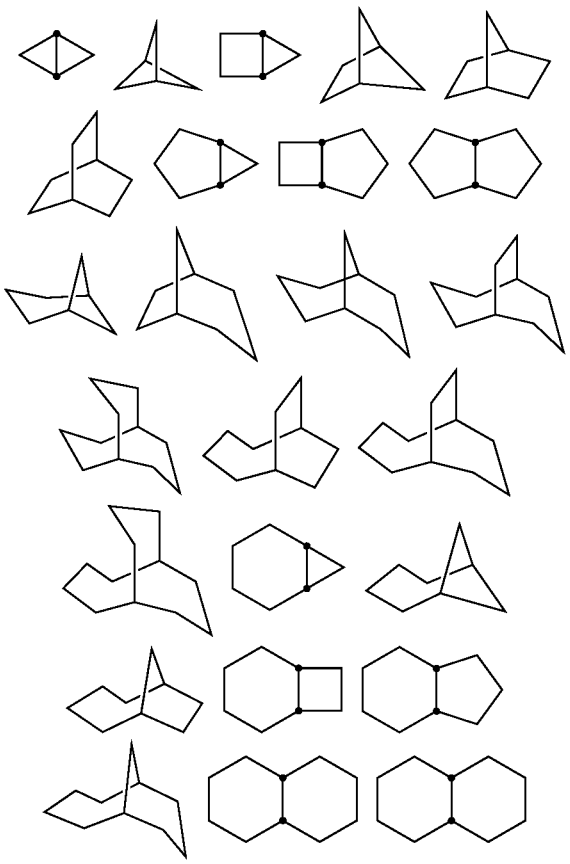

Bicyclic ring systems can be optionally substituted with one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like. Examples of substituted bicyclic ring systems include camphor, 1,7,7-trimethylbicyclo[2.2.1]heptane, 3-cadinene, and steroids such as e.g., cholesterol, cholic acid, cortisone, testosterone, estradiol, and progesterone.

The term "aryl" or "Ar", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "aralkyl", alone or in combination, means an alkyl or cycloalkyl radical as defined herein in which one hydrogen atom is replaced by an aryl radical as defined herein, such as benzyl, 2-phenylethyl, and the like.

The term "heterocyclic" or "heterocycloalkyl" group means ring structures containing at least one other kind of atom, in addition to carbon, in the ring. The most common of the other kinds of atoms include nitrogen, oxygen and sulfur. Heterocyclic systems include 3, 4, 5, 6, 7 and 8-membered monocyclic ring systems. A heterocyclic group can have one or more carbon-carbon double bonds or carbon-heteroatom double bonds in the ring so long as the ring is not rendered aromatic by their presence. Examples of heterocyclic groups include, but are not limited to, aziridineyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocyclic group can be unsubstituted or substituted with one or more suitable substituents.

The terms "aryl heterocycles", "heteroaryls" or "heteroaromatics" refer to those aryl groups having heteroatoms in the ring structure. The aromatic ring can be substituted at one or more ring positions with substituents for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The term "ester" includes compounds and moieties which contain a carbon bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "hydroxy" or "hydroxyl" includes groups with an —OH or —O.

The term "halogen" includes fluorine, bromine, chlorine, iodine, etc. The term "perhalogenated" generally refers to a moiety wherein all hydrogens are replaced by halogen atoms.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

It will be noted that the structure of some of the compounds of the invention include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this invention may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers or atropisomers (rotational isomers) thereof. "Atropic isomers" are a type of stereoisomer in which the atoms of isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases. Below is an illustration of atropisomers of meso-tetrakis-(N-alkylpyridinium-2-yl)-porphyrin.

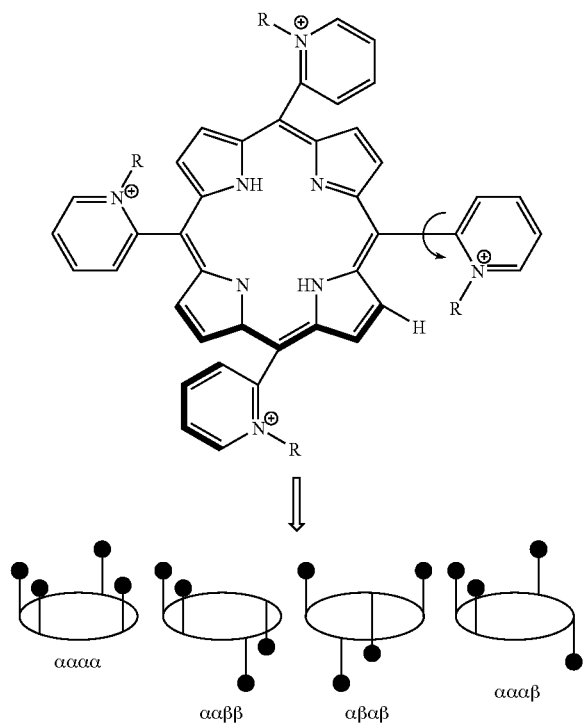

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions. For example, using different solvents or different solvent mixtures for recrystallization; crystallization at different temperatures; various modes of cooling, ranging from very fast to very slow cooling during crystallization, and the like. Polymorphs are also obtained by heating or melting the disclosed compounds followed by gradual or fast cooling. The presence of polymorphs is determined by solid probe nuclear magnetic resonance spectroscopy, infrared spectroscopy, differential scanning calorimetry, powder X-ray diffraction, and other techniques known to one skilled in the art.

Additionally, the compounds of the present invention, for example, the salts of the compounds, can exist in either the hydrated or unhydrated (anhydrous) form or as solvates with other solvent molecules. Non-limiting examples of hydrates include monohydrates, dihydrates, etc. Non-limiting examples of solvates include ethanol solvates, acetone solvates, etc.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples include:

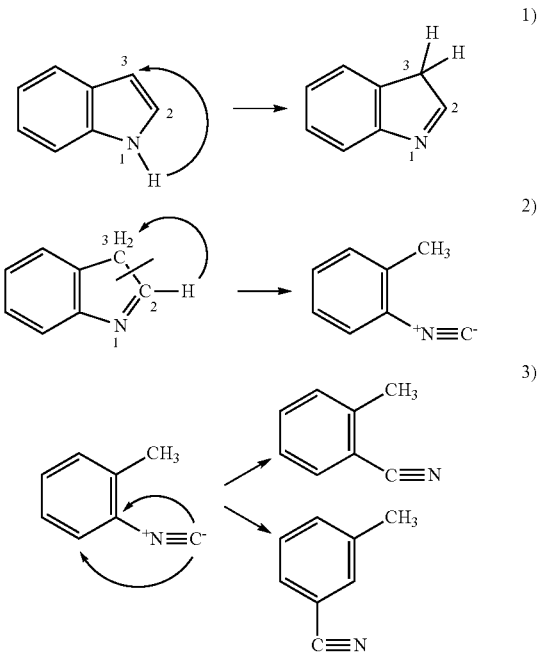

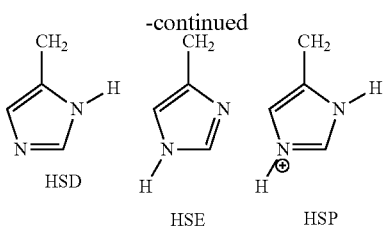

HSD  HSE  HSP

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The term "2-PyP" refers to a porphyrin substituted with 2-pyridyl substituents e.g.,

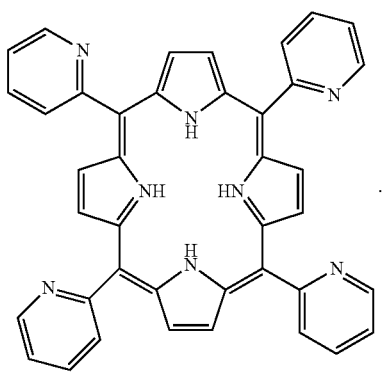

The term "metal(s)" refers to any atom of the Periodic Table having the properties of a metal. These include preferably all transition metals, actinides and lanthanides. More preferably tin, silicon, germanium, copper, iron, cobalt, zinc, nickel or manganese are used. See *Porphyrins and Metalloporphyrins* by K. M. Smith, Elsevier/North-Holland Biochemical Press (1976), which is incorporated herein in its entirety by reference. "Metal salt" refers to an organic or inorganic salt used to treat a dihydro-porphyrin compound to produce the corresponding metal porphyrin compound. Acetates and propionates are preferred.

The term "pharmacologically effective amount" as used herein means an amount that slows or prevents the progression of the targeted disease or pathology. It is preferable that the slowing or prevention not be accompanied by a toxic effect that offsets the medical value of slowing or preventing the progression of the targeted disease or pathology.

The "pharmaceutically acceptable carrier" must be "acceptable" in the sense of being compatible with the compounds or compositions of the invention and not deleterious to the subject to be treated. Preferably, the carrier is also capable of stabilizing the compound or composition.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, lhydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be formed from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used.

The number of atoms protonated and counterions associated with the salt can be controlled and depends on the number of acidic/basic atoms in the parent compound and amount of acid which is used to treat the parent compound. In one embodiment of the invention, the monohydrochloride salt of the parent compound is formed upon treatment with hydrochloric acid. In another embodiment, the dihydrochloride salt of the parent compound is formed upon treatment with hydrochloric acid.

Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxylamine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formulae I, and the like, See Bundegaard, H. "Design of Prodrugs" p 1-92, Elesevier, New York-Oxford (1985).

In one embodiment, the compound is based on a porphyrin structure. As used herein, the term "porphyrin" includes compounds prior to a metal atom being inserted into the ring system, as well as molecular systems in which compounds are attached to the metal. The substituents, as well as the overall porphyrin structure, can be neutral, positively charged, or negatively charged.

Synthesis of Peroxynitrite Decomposition Catalysts

In various embodiments, the macrocyclic compounds of the invention are provided as a metallic complex. The metallic complexes can be, e.g., porphyrin-iron, porphyrin-manganese, or porphyrin-zinc complexes.

Starting porphyrins can be prepared according to methods well known in the art. The methods can include, for example, those described in WO95/31197, Campestrini and Meunier, Inorg. Chem. 31, 1999-2006, (1992); Robert et al., Inorg. Chem. 30, 706-711, (1991); Lindsey and Wagner, J. Org. Chem. 54, 828-836, (1989); and Zipplies, et al., J. Am. Chem. Soc. 108, 4433-4445, (1986). See, also, Meltze; Phthalocyanine Technology in Chemical Process Reviews No. 42; Noyes Data Corp. Park Ridge, N.J. (1970). See, also, Goedken, et al., J.C.S. Chem. Comm. 337-338, (1973); Martin, and Cummings, Inorg. Chem. 12, 1477-1482, (1973); Riley, et al., J. Am. Chem. Soc. 98, 1752-1762, (1976); Dabrowiak, et al., J. Am. Chem. Soc. 95, 6613-6622, (1973); Riley and Busch, Inorg. Chem. 23, 3235-3241, (1984); Watkuns, et al., Inorg. Chem. 15, 387-393, (1976); and Riley, et al., J. Am. Chem. Soc. 99, 767-777, (1977). Pyridinium porphyrins can also be synthesized as described in Hunt et al., in Chem. & Biol. 4:845-58, 1997. Substituted porphyrins can also be synthesized as described herein.

Where a substituent is designated as, or can be, a hydrogen, the exact chemical nature of a substituent which is other than hydrogen at that position, e.g., a hydrocarbonyl radical or a halogen, hydroxy, amino and the like functional group, is not critical so long as it does not adversely affect the overall activity and/or synthesis procedure. Where a ligand ($L_1$ and $L_2$) or a charge neutralizing anion is designated as a particular chemical entity, the exact chemical nature of a ligand or a charge neutralizing anion which is other than the particular chemical entity depicted is not critical so long as it does not adversely affect the overall activity and/or synthesis procedure.

Properties of the 2-pyridyl compounds of the invention can be determined using methods known in the art. For example, methods for determining pKa, electronic absorption spectra, phosphate binding, cyanide binding, EPR spectroscopy in the presence of increasing KCN concentrations, magnetic susceptibility, ascorbate reduction, and electrochemical reduction are described in methods for electronic spectral, magnetic and electrochemical properties of imidazolyl-containing compounds as described in D. E. Lahaye, *Water-Soluble meso Imidazolyl Manganese Porphyrins Biomimetics and Oxidation Catalysis*, Doctoral Dissertation, Princeton University, 2005.

Synthesis of Amphiphilic Catalysts and Preparation of Vesicular Assembly Systems According to the Invention The invention includes amphiphilic compounds. In one embodiment, the amphiphic compound contains a metallic complex, e.g., a metallic porphyrin compound. Porphyrin compounds can be synthesized as described generally in Hunt et al., in Chem. & Biol. 4:845-58, 1997. Substituted metallic complex amphiphiles within the invention are prepared by methods known in the art. Polyether cascade dendritic porphyrins can be prepared resulting in a symmetrical solution dendrimer. If desired, unsymmetrical derivatives with a single hydrophobic side chain can be readily prepared by procedures known in the art. While not wishing to be bound by theory, it is believed the side chains of the invention ($R_1$, $R_2$, $R_3$, and $R_4$ when present) lower toxicity by minimizing or preventing liver uptake, thereby allowing the compound to be maintained longer in a subject's blood pool. If desired, targeting agents such as steroids can be attached.

Amphiphilic porphyrin compound analogs can include end products synthesized using procedures generally described Hunt et al., in Chem. & Biol 4:845-58, 1997. For example, iron and manganese porphyrins can be constructed by using as starting materials pyridinium porphyrins that are synthesized according to methods known to those skilled in the art and referenced above. For example, pyridinium porphyrins can be synthesized by peralkylation of 5,10,15,20,-tetrakis(4-pyridyl)porphine with an appropriate alkyl iodide, e.g., dodecyl iodide.

Porphyrins preferably are located in a hydrophilic environment for the efficient catalysis of peroxynitrite. Thus, in preferred embodiments, the invention includes PEG-linked (polyethylene glycol) substituted porphyrin compounds. In certain aspects of the invention, these porphyrins can be provided in vesicular assemblies, such as liposomes. In such an environment, the PEG-linkers extend the metalloporphyrin head group away from the interfacial region between the membrane and external solution and further into the bulk solvent. The hydrophilicity of the porphyrin head group correlates with the efficiency of the catalysts: the rate of peroxynitrite decomposition is much faster when catalyzed by PEG-linked metalloporphyrins, as compared to metalloporphyrins with simple dodecyl chains. In some embodiments, tocopherol, e.g., α tocopherol or, preferably, γ tocopherol, is also present in the vesicular assembly.

The compounds can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, including by formation of diastereoisomeric salts through treatment with an optically active acid (e.g., tartaric, diacetyltartaric, dibenzoyltartaric, ditoluoyltartaric and camphorsulfonic) and then separation of the mixture of diastereoisomers by crystallization followed by liberation of the optically active bases from these salts. Another process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The chemical reactions shown by the references described above are generally disclosed in terms of variations appropriate for their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, or the like. Alternatively, other reactions disclosed herein or otherwise conventionally known, will be applicable to the preparation of the corresponding compounds of this invention. In all preparative methods, all starting materials are known or can be readily prepared from known starting materials.

Additional methods for synthesizing compounds according to the invention are described in the Examples, below.

Screening Compounds for Catalytic Activity

To screen compounds for peroxynitrite decomposition catalytic activity of the invention, peroxynitrite is prepared and isolated as its sodium salt by the reaction of acidic hydrogen peroxide with sodium nitrite followed by rapid quenching with NaOH as set out by Halfpenny and Robinson, in *J. Chem. Soc.*, 928-938 (1952). Peroxynitrite has an absorbance maximum at 302 nm with an extinction coefficient of 1670 $M^{-1}$ $cm^{-1}$. Therefore, it is possible to directly observe the decomposition of peroxynitrite by monitoring the change in absorbance at 302 nm by stop-flow spectrophotometric analysis. For example, the decomposition of peroxynitrite at an accelerated rate (relative to the natural decomposition rate of peroxynitrite) upon the addition of the decomposition catalysts of the invention.

In addition, it is known that peroxynitrite inactivates CuZn-SOD (superoxide dismutase) enzyme in a concentration dependant manner. Peroxynitrite is also reported to inactivate Mn-SOD. See Ischiropoulos et al., *Archives of Biochemistry and Biophysics*, 298:2, 431-437 (1992). The invention provides compounds and methods for screening for compounds which protect CuZn-SOD or Mn-SOD by inactivating peroxynitrite.

Peroxynitrite catalytic activity can also be measured using methods described in Hunt et al., Chem. & Biol. 4:845-58, 1997.

Pharmaceutical Compositions

The pharmaceutical compositions of the invention include a pharmaceutically effective amount of one or more of the compounds of the invention administered in a dosage regimen appropriate for treating a disease condition. The dosage regimen is selected in accordance with a variety, of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For example, total daily dose administered to a mammal in single or divided doses may be in amounts, for example, from about 1 to about 100 mg/kg body weight daily and more usually about 3 to 30 mg/kg. Dosage unit compositions may contain such amounts of submultiples thereof to make up the daily dose. The number of submultiples is preferably about one to three times per day of about 30 mg/kg per unit dosage form. The serum concentrations of the doses are about 1 pM to 1.5 pM, e.g., 3 pM-1.0 µM, 300 pM to 750 nM, 500 pM to 250 nM, or 1 nm to 125 nM. Furthermore, the amount of active ingredient that may be combined with the carrier materials to produce a single dosage form will vary depending upon the host treated and the particular mode of administration.

The invention also includes pharmaceutical compositions suitable for decomposing peroxynitrite in a cell both in vivo and in vitro. More preferably, the invention includes pharmaceutical compositions suitable for decomposing peroxynitrite under physiological conditions. The compositions are preferably suitable for internal use and include an effective amount of a pharmacologically active compound of the invention, alone or in combination, with one or more pharmaceutically acceptable carriers. The compounds are especially useful in that they have very low, if any toxicity.

In practice, the compounds of the inventions or their pharmaceutically acceptable salts, are administered in amounts which will be sufficient to inhibit inflammatory conditions or disease and/or prevent the development of inflammation or inflammatory disease in animals or mammals, and are used in the pharmaceutical form most suitable for such purposes.

Preferred pharmaceutical compositions are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient. Administration of the active metallic complexes of the inventions and salts described herein can be via any of the accepted modes of administration for therapeutic agents. These methods include systemic or local administration such as oral, nasal, parenteral, transdermal, subcutaneous, or topical administration modes.

Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages. The compositions will include an effective amount of active compound of the invention or the pharmaceutically acceptable salt thereof, and in addition, and may also include any conventional pharmaceutical excipients and other medicinal or pharmaceutical drugs or agents, carriers, adjuvants, diluents, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The compounds of the invention may be also formulated as suppositories using for example, polyalkylene glycols, for example, propylene glycol, as the carrier.

Liquid, particularly injectable compositions can, for example, be prepared by dissolving, dispersing, etc. The compound of the invention is dissolved in or mixed with a pharmaceutically pure solvent such as, for example, water, saline, aqueous dextrose, glycerol, ethanol, and the like, to thereby form the injectable solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One approach for parenteral administration employs the implantation of a slow-release or sustained-released systems, which assures that a constant level of dosage is maintained, according to U.S. Pat. No. 3,710,795.

The compounds of the invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the invention, when used for the indicated effects, will range between about 0.05 to 1000 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Effective plasma levels of the compounds of the invention range from 0.002 mg to 50 mg per kg of body weight per day.

Compounds of the invention may be administered in a single daily dose, or the total daily dosage may be administered in divided doses of two, three or four times daily. Furthermore, compounds for the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the invention may also be delivered by the use of monoclonal antibodies as individual carriers to which the metallic complex molecules are coupled. The compounds of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the metallic complexes of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. Any of the above pharmaceutical compositions may contain 0.1-99%, preferably 1-70% of the active compound.

While the compounds of the invention can be administered as the sole active pharmaceutical agent, they can also be used in combination with one or more compounds of the invention or with one or more compounds which are known to be effective against the specific disease state that one is targeting for treatment.

Therapeutic Methods

The invention also provides methods for preventing or reducing cellular damage resulting from exposure to various chemical compounds which produce potentially damaging free radical species, comprising administering a therapeutically or prophylactically efficacious dosage of at least one species of a substituted compound of the invention, e.g., a substituted metalloporphyrin.

Compositions including the herein described compounds may be administered for various indications, including: (1) for preventing ischemic reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens, and (6) for prophylactic administration to prevent: carcinogenesis, cellular senescence, cataract formation, formation of malondialdehyde adducts, HJV pathology and macromolecular crosslinking, such as collagen crosslinking. In one aspect of the invention, compounds of the invention are formulated for administration by the oral route by forming a pharmaceutical dosage form comprising an excipient and not less than 1 microgram nor more than about 10 grams of at least one antioxidant complex of the invention. Dietary formulations are administered for therapy of free radical-induced diseases and/or for the chemoprevention of neoplasia and/or oxidative damage associated with normal aerobic metabolism.

In another aspect, buffered aqueous solutions comprising one or more antioxidant substituted compounds of the invention at a concentration of at least 1 nM but not more than about 100 mM is formulated for administration, usually at a concentration of about 0.1 to 10 mM, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, (7) hyperbaric oxygen, or (8) apoptosis of a predetermined cell population (e.g., lymphocyte apoptosis). Administration can be via any desired route, e.g., intravenous, subcutaneous, inhalation, intramuscular. The buffered aqueous solutions may also be used, typically in conjunction with other established methods, for organ culture, cell culture, transplant organ maintenance, and myocardial irrigation. Non-aqueous formulations, such as lipid-based formulations are also provided, including stabilized emulsions. The invention also encompasses pharmaceutical compositions of compounds of the invention, therapeutic uses of such compounds, methods and compositions for using these compounds in diagnostic, therapeutic, and research applications in human and veterinary medicine.

Another aspect of the invention is its use in enhancing the recovery of skin of a warm-blooded animal from wounds, such as surgical incisions, burns, inflammation or minor irritation due to oxidative damage, etc. This method includes administering to the skin wound or irritation a therapeutically or, in some cases a prophylactically effective amount of a composition which comprises a compound of the invention as described herein. Additionally, the invention provides a method of treating a peroxide-induced condition in a subject which comprises administering to the subject an amount of any of the compounds of the invention effective to reduce peroxide in a subject and thereby treat the peroxide-induced condition. Administration of the compound to the subject may be effected by means other than those listed herein. Further, the peroxide-induced condition may involve cataracts, inflammation of a tissue, ischemia, an allergic reaction, or pathology caused by oxidative stress. Where the peroxide-induced condition involves cataracts, administration is effected by, but is not limited to, topical contact to the surface of an eye.

The method includes contacting the cell with any compound of formula I in a pharmaceutically effective amount, that is, sufficient to actively decompose peroxynitrite in the cell. In general, any cell having peroxynitrite, or capable of synthesizing peroxynitrite, can be treated. The cell can be provided in any form so long as it is accessible to the compound. For example, the cell can be provided in vitro, ex vivo, or in vivo. Peroxynitrite decomposition can be measured using any method known in the art, e.g., methods such as stopped-flow kinetic analysis.

Also provided in the invention is a method of inhibiting, preventing, or treating a pathology advantageous affected by the decomposition of peroxynitrite in a mammal. The disease or pathology can be associated, e.g., with an inflammatory disease or neurodegenerative disease characterized by the presence of peroxynitrite. Inflammatory diseases refer to diseases or conditions where there is an inflammation of the body tissue. Neurodegenerative diseases refer to diseases causing the breakdown of neural tissue and/or function. These both include local inflammatory responses and systemic inflammation. Examples of such diseases and conditions include: complications of organ transplantation including lung transplantation, including bronchitis, including obliterative bronchitis; chronic inflammatory disorders of the joints, including arthritis, rheumatoid arthritis, osteoarthritis and bone diseases associated with increased bone resorption; inflammatory bowel diseases such as ileitis, colitis, including ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gum, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis and viral or autoimmune encephalitis; autoimmune diseases such as diabetes, including diabetic neuropathy, vascular complications of diabetes, and diabetes mellitus, immune-complex vasculitis, systemic lupus erythematosus (SLE); inflammatory diseases of the heart such as cardiomyopathy, ischemic heart disease, hypercholesterolemia, atherosclerosis, doxorubicin-induced cardiac dysfunction; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines.

The invention also includes a method of treating, preventing, or otherwise inhibiting reperfusion injury in a subject in need of treatment, prevention, or inhibition thereof. The method includes administering a peroxynitrite decomposition catalyst i.e., a compound of the invention as disclosed herein in an amount sufficient to inhibit reperfusion injury in the subject. Reperfusion refers to the process whereby blood flow in the blood vessels is resumed after blood flow has been interrupted, such as occurs following constriction or obstruction of the vessel. Reperfusion is typically associated with ischemia and may result following a naturally occurring episode, such as a myocardial infarction or stroke, or during a surgical procedure where blood flow in vessels is purposely or unintentionally blocked off.

The subject in the above-mentioned methods can be, e.g., a mammal, e.g., a human, mouse, rat, dog, cat, horse, cow, pig, or non-human primate. Administration can be systemic or topical, and can be prophylactic or therapeutic.

EXAMPLES

The invention will be further described in the following examples, which do not limit the scope of the invention described in the claims.

Example 1

Synthesis of zinc(II)-2-TRMBzPvP

Synthesis of R-(+)-methylbenzybromoacetamide

Liu, S.; Pietryka, J.; Ellars, C. E.; Edwards, D. S. *Bioconjugate Chem.* 2002, 13, 902-913

To 20 mL of dry dioxane was added 0.48 g (3.47 mmol) bromoacetic acid and 0.39 g (3.47 mmol) N-hydroxysuccinimide. DCC, 0.79 g (3.82 mmol) was dissolved in 10 mL dioxane and added via pipette to the stirred solution. Dicyclohexylurea precipitated as a milky solid and was filtered off after 2 hr. (R)-(+)-methylbenzylamine, 0.37 g (3.13 mmol) was added to the filtrate and the mixture was stirred for 5 hr, until the reaction was complete by tlc. The dioxane was removed and the residue was taken up in EtOAc, and the organic layer was washed with 40 mL 10% citric acid, 40 mL $NaCO_3$, and brine. The organic layer was dried over $Na_2SO_4$ and the solvent was removed to leave (R)-(+)-methylbenzylbromoacetamide (5) as a white solid. Purification by column chromatography (2:8 EtOAc:$CH_2Cl_2$) left the bromoacetamide in 80% yield as a fluffy white solid. EI-MS: parent ion peak at 242 (Calculated mass 242). $^1$H NMR (CDCl$_3$, 300 MHz) δ1.55 (d, 3H, J=7.0 Hz, CHCH$_3$) δ3.89 (dd, 2H, J=17.0 Hz, BrCH$_2$CO) 55.10 (quintet, 1H, J=7.0 Hz, CHCH$_3$) δ6.8 (br s, 1H, NH) 57.3 (m, 5H, phenyl)

Synthesis of 2-tetrakis-(N—R-(+)-methylbenzylacetamido)-pyridyl porphyrin

To 3 mL of anhydrous DMF under $N_2$ was added 25 mg (0.04 mmol) 2-PyP and 1 g (4.12 mmol) (R)-(+)-methylbenzylbromoacetamide. The reaction was allowed to stir at 100-110° C. for 6 hr, until $\lambda_{max}$ had shifted from λ=418 nm to λ=422 nm and an aliquot of reaction mixture partitioned between CHCl$_3$ and H$_2$O showed no color in the water layer. The reaction mixture was cooled and dropped into rapidly stirred ether, then filtered. The precipitated porphyrin was dissolved in 10 mL H$_2$O and extracted with 2×20 mL CHCl$_3$, then precipitated by the addition of a concentrated solution of NH$_4$PF$_6$ in H$_2$O. The hexafluorophosphate salt of the porphyrin was filtered off and washed with H$_2$O. This salt was then dissolved in acetone and applied to a 3×12 cm column of normal phase silica gel packed in 8:1:1 CH$_3$CN:H$_2$O:sat. aq. KNO$_3$. Fractions with R$_f$=0.63 were collected. The appropriate fractions were concentrated until the porphyrin just began to precipitate, then just enough CH$_3$CN was added to the solution to re-dissolve the porphyrin. A saturated solution of NH$_4$PF$_6$ in H$_2$O was then added, and the porphyrin precipitated as a fine powder, which could be filtered onto Celite and washed. The hexafluorophosphate salt of 2-TMBzPyP was isolated as a red-purple solid in 32% yield. High-Resolution ESI-MS: {2-TRMBzPyP-H}$^3$ (m/z=421.8642 Calculated=421.8625)

Synthesis of zinc(II)-2-TRMBzPyP

ααββ-2-TRMBzPyP, 15 mg (9.5×10$^{-3}$ mmol) and zinc(II) acetate, 20.7 mg (0.095 mmol) were dissolved in a mixture of water and methanol and stirred at room temperature overnight. The formation of the zinc porphyrin was confirmed by a shift in the porphyrin soret from 422 to 434 nm in methanol. The solvent was evaporated and the porphyrin was purified by double precipitation as described in the synthesis of the Mn(III)porphyrin.

ESI-MS data: 455 {Zn-2-TRMBzPyP-Cl}$^3$ (calculated m/z 455.2) and 701 {Zn-2-TRMBzPyP-2Cl}$^{2+}$ (calculated m/z 700.6). UV-visible (water, pH 9.09 borate buffer): $\lambda_{max}$ (log$_{10}$ε) 431(5.27) 560(4.12) 594(3.64)

Example 2

Synthesis of zinc(II)-2-TRBor PyP

Synthesis of R-(+)-bornylbromoacetamide

Bromoacetic acid, 503 mg (3.62 mmol), N-hydroxysuccinimide, 417 mg (3.62 mmol) and DCC, 823 mg (3.98 mmol) were dissolved in 50 mL dioxane in an oven dried flask and stirred for an hr. After an hr the reaction mixture was filtered and 500 mg (3.26 mmol) R-(+)-bornylamine was added to it. The reaction mixture was stirred overnight and the reaction was stopped when there was no unreacted starting material as checked by TLC. The solvent was evaporated and the residue was redissolved in ethyl acetate and washed with 10% citric acid, 5% sodium carbonate and saturated NaCl solutions. The organic layer was dried over sodium sulfate and evaporated to give the crude product which was purified by silica gel column chromatography (1:9 EtOAc:CH$_2$C$_2$) to yield 847 mg (94%) R-(+)-bornylbrornoacetamide.

Synthesis of 2-tetrakis-(N—R-(+)-bornylacetamido)-pyridyl porphyrin

2-PyP, 25 mg (0.04 mmol) and R-(+)-bornylbromoacetamide, 517 mg (1.88 mmol) were dissolved in 5 mL dry DMF in an oven dried and flame dried flask. The reaction mixture was heated to 100° C. and stirred for 27 hr under argon atmosphere. The reaction was monitored by UV-Visible spectroscopy by removing aliquots of the reaction mixture and dissolving in methanol. The porphyrin soret band shifted from 412 nm to 420 nm during the course of the reaction. The reaction mixture was cooled to room temperature and added dropwise to 50 mL anhydrous ethyl ether. The crude product precipitated and was collected by filtration over celite and dissolved in methanol. The solvent was evaporated and the residue redissolved in minimum volume of water. The product was reprecipitated with ammonium hexafluorophosphate and collected by filtration over celite. The product was dissolved in acetone and the solvent was stripped. Residual water was evaporated by azeotroping with methanol. The residue was dissolved in minimum volume of acetone and reprecipitated with tetra-butyl ammonium chloride. The product was collected by filtration over celite, washed with acetone to remove excess tetra-butyl ammonium chloride and dissolved in methanol. The solvent was stripped to give the crude product which was purified by semi-preparative HPLC to give pure 25 mg (47%) (ααββ-tetra-(R-bornylacetamido)-2-pyridylporphyrin. High-Resolution ESI-MS: {2-TRBor PyP-H$^+$}$^{3+}$ (m/z=464.6136 Calculated=464.6126)

Synthesis of zinc(II)-2-TRBor PyP

ααββ-2-TRBor PyP, 10 mg (5.83×10$^{-3}$ mmol) and zinc(II) acetate, 13 mg (0.0583 mmol) were dissolved in a mixture of water and methanol and stirred at room temperature overnight. The formation of the zinc porphyrin was confirmed by a shift in the porphyrin soret from 422 to 436 nm in methanol. The solvent was evaporated and the porphyrin was purified by double precipitation as described in the synthesis of the Mn(III)porphyrin. ESI-MS data: 498 {Zn-2-TRBor PyP-Cl}$^{3+}$ (calculated m/z 498.2) and 764 {Zn-2-TRBor PyP-2Cl}$^{2+}$ (calculated m/z 764.6). UV-visible (water, pH 9.54 borate buffer): $\lambda_{max}$ (log$_{10}$ε) 430(4.93) 560(3.85) 595(3.44)

Example 3

Synthesis of Iron(III) chloride meso-tetrakis-2-(N-(2-methoxy)ethyl)pyridyl porphyrin

Synthesis of 2-methoxyethyl tosylate 2-methoxyethanol (0.989 g, 13 mmol) was dissolved in 30 ml dichloromethane, and triethylamine (2.53 g, 25 mmol) was added to the solution. The reaction mixture was set to stir in an ice-water bath, and p-toluenesulfonyl chloride (3.22 g, 17 mmol) was added all at once. The ice was allowed to melt, and the reaction was continued overnight. The reaction mixture was then filtered, to remove all of the triethylamine hydrochloride, and the filtrate was washed with ml saturated NaHCO$_{3(aq)}$, then 30 ml 1N KHSO$_{4(aq)}$, then 30 ml saturated NaHCO$_{3(aq)}$. The organic layer was dried over anhydrous magnesium sulfate, and the solvent was removed by distillation. The colorless oily residue was chromatographed on silica gel in 1:5 ethyl acetate:chloroform, to yield 2.77 g (92% yield) of 2-methoxyethyl tosylate as a viscous liquid.

$^1$H NMR (300 MHz, CDCl$_3$): δ2.4 (s, 3H, ArCH$_3$), δ3.3 (s, 3H, —OCH$_3$), δ3.6 (m, 2H, —CH$_2$OCH$_3$), δ4.1 (m, 2H, —CH$_2$OSO$_2$ Ar), δ7.3 (d, J=8.5 Hz, 2H, —SO$_2$CHCHCCH$_3$), δ7.8 (d, J=8.5 Hz, 2H, —SO$_2$CHCHCCH$_3$).

Synthesis of meso-tetrakis-2-(N-(2-methoxy)ethyl)pyridyl porphyrin

In an oven-dried flask under argon, were combined meso-tetrakis-2-pyridyl porphyrin (2-PyP; 0.091 g, 0.148 mmol) and 2-methoxyethyl tosylate (1.33 g, 5.77 mmol) in 1.37 ml anhydrous DMF. The reaction mixture was heated to 100° C. and stirred for 18 h 30 min. Reaction progress was monitored by reverse-phase HPLC. Once complete, the reaction mixture was cooled to room temperature before being added dropwise to diethyl ether, to precipitate out the product and remove DMF and excess alkylating agent. The porphyrin was filtered onto Celite and washed off with water. The porphyrin was precipitated from water as the hexafluorophosphate salt with saturated NH$_4$PF$_{6(aq)}$ added dropwise. The porphyrin was again filtered onto Celite, and washed off with acetone. Saturated tetrabutylammonium chloride (in acetone) was added dropwise to precipitate out the porphyrin as the chloride salt. The gummy precipitate was again filtered onto Celite and washed well with dry acetone, to thoroughly remove any lingering salts, and finally washed off with methanol. The porphyrin was then chromatographed on Sephadex LH-20 in 1:1 methanol:water as the eluant, and collection of appropriate fractions yielded meso-tetrakis-2-(N-(2-methoxy)ethyl) pyridyl porphyrin in 65% yield. $^1$H NMR (300 MHz, CD$_3$OD): δ2.8-3.0 (singlets, 12H, —CH$_2$OCH$_3$), δ3.2-3.4 (m, 8H, —CH$_2$OCH$_3$), δ4.5-4.8 (m, 8H, N$^+$CH$_2$), δ8.6 (m, 4H, N$^+$CHCH), δ8.8-9.1 (m, 8H, N$^+$CHCHCH and N$^+$CCH), δ8.8-9.4 (br s, 8H, pyrrole), δ9.5 (m, 4H, N$^+$CH). Partial UV-Vis (H$_2$O) (log ε): 417 (5.31).

Synthesis of Iron(III) chloride meso-tetrakis-2-(N-(2-methoxy)ethyl)pyridyl porphyrin Free base meso-tetrakis-2-(N-(2-methoxy)ethyl)pyridyl porphyrin (0.055 g, 0.055 mmol) was dissolved in 10 ml deionized water, ferrous ammonium sulfate hexahydrate (0.018 g, 0.295 mmol) was added, and the reaction mixture was refluxed until the porphyrin Soret shifted to 412 nm and the number of Q bands had reduced from 4 to 2 (approximately 10 h). The reaction mixture was cooled to room temperature, and BioRad AG1X8 chloride ion exchange resin (0.501 g) was added and allowed to stir for 2 h. The resin was filtered off, the filtrate was neutralized, and the solvent was removed by distillation. The residue was chromatographed on Sephadex LH-20 in 1:1 methanol:water as the eluant. Collection of appropriate fractions yielded iron(III) chloride meso-tetrakis-2-(N-(2-methoxy)ethyl)pyridyl porphyrin in 99% yield. Partial UV-Vis (H$_2$O) (log ε): 412 (4.76).

Example 4

Synthesis of Iron(III) chloride meso-tetrakis-2-(N-2-methoxyethylacetamido)pyridyl porphyrin

Synthesis of 2-methoxyethylbromoacetamide 2-methoxyethylamine (0.750 g, 10 mmol) was dissolved in 50 ml dichloromethane in a 100-ml round-bottom flask, and cooled in an ice-water bath. Bromoacetyl bromide (1 g, 5 mmol) was added dropwise via syringe, and the reaction was continued overnight. The reaction mixture was added to 260 ml ethyl acetate and 2.5 ml dichloromethane, and the solution was washed with two portions each of water and of saturated $NaCl_{(aq)}$. The organic layer was dried over anhydrous magnesium sulfate, and the solvent was removed by distillation to leave 0.64 g of 2-methoxyethylbromoacetamide (66% yield) as a yellow oil.

$^1$H NMR (300 MHz, CDCl$_3$): δ3.36 (s, 3H, OCH$_3$), δ3.415 (m, 4H, CH$_2$H$_2$OCH$_3$), δ3.87 (s, 2H, BrCH$_2$CO), δ6.8 (br s, 1H, NH).

Synthesis of meso-tetrakis-2-(N-2-methoxyethylacetamido)pyridyl porphyrin

In an oven- and flame-dried flask under argon, were combined 2-PyP (0.015 g, 0.024 mmol) and 2-methoxyethylbromoacetamide (1.0 g, 5.10 mmol) in 2.5 ml anhydrous DMF. The reaction mixture was heated to 90-100° C. and stirred for 8 h, by which time the Soret had shifted to 418 nm (H$_2$O), cooled to room temperature, and added dropwise to rapidly stirred diethyl ether to precipitate the porphyrin. The solid was filtered and washed well to yield meso-tetrakis-2-(N-2-methoxyethylacetamido)pyridyl porphyrin as a sticky purple solid.

$^1$H NMR (300 MHz, CD$_3$OD): δ2.0-3.0 (singlets and unresolvable protons, 7H, CONHCH$_2$CH$_2$OCH$_3$), δ8.8 (t, 1H, N$^+$CHCH), 58.9-9.4 (br s, 2H, pyrrole), 59.1 (t, 1H, N$^+$CHCHCH), δ9.2 (t, 1H, N$^+$CCH), δ9.56 (q, 1H, N$^+$CH).

Synthesis of iron(III) chloride meso-tetrakis-2-(N-2-methoxyethylacetamido)pyridyl porphyrin Free base meso-tetrakis-2-(N-2-methoxyethylacetamido) pyridyl porphyrin was dissolved in deionized water, ferrous ammonium sulfate hexahydrate was added, and the reaction mixture was refluxed until the porphyrin Soret shifted to 412 nm and the number of Q bands had reduced from 4 to 2. The reaction mixture was cooled to room temperature, and Bio-Rad AG1X8 chloride ion exchange resin was added and allowed to stir for 2 h. The resin was filtered off, the filtrate was neutralized, and the solvent was removed by distillation. The residue was chromatographed on Sephadex LH-20 in 1:1 methanol:water as the eluant. Collection of appropriate fractions yielded iron(III) chloride meso-tetrakis-2-(N-2-methoxyethylacetamido)pyridyl porphyrin.

Example 5

Synthesis of Iron(III) chloride meso-tetrakis-2-(N-(2-methoxyethyl)acetamido)pyridyl porphyrin Synthesis of 2-bromo-N-(2-methoxyethyl)acetamide 2-methoxyethylamine (3.73 g, 0.0496 mol) was dissolved in dichloromethane (250 ml) and cooled to 0° C. Bromoacetyl bromide (2.16 ml, 0.0248 mol) was added dropwise, and the reaction was stirred overnight at room temperature. The reaction mixture was then washed with water (100 ml) and saturated aqueous sodium chloride (2×100 ml). The organic layer was separated and dried over anhydrous sodium sulfate, and the solvent was evaporated under reduced pressure to afford 2-bromo-N-(2-methoxyethyl)acetamide as a white solid in 75% yield.

$^1$H NMR (300 MHz, CDCl$_3$): δ3.4 (s, 3H, OCH$_3$), δ3.5 (m, 4H, NHCH$_2$CH$_2$OCH$_3$), δ3.9 (s, 2H, BrCH$_2$), δ6.8 (br s, 1H, NH).

MP (° C.): 33

Synthesis of meso-tetrakis-2(N-(N-(2-methoxyethyl)acetamido)pyridyl porphyrin

2-PyP (0.081 g, 1.31×10$^{-4}$ mol) and 2-bromo-N-(2-methoxyethyl)acetamide (1.0 g, 5.1×10$^{-3}$ mol) were added to a microwave vial previously purged with Ar (0.5-2 ml size) and equipped with a stir bar. The vial was sealed with the provided cap, which was crimped on tightly. The vial was then heated in an oil bath at 100° C. and stirred for 3 h. HPLC, monitoring $A_{418}$, was used to monitor the progress of the alkylation of 2-PyP, and to separate the major tetraalkylated products from one another for identification purposes, as we have previously described See, Datta, A.; Quintavalla, S. M.; Groves, J. T., Unusual Alkylation Selectivity in the Synthesis of Water-soluble 2-pyridyl porphyrins: Kinetic versus Thermodynamic Control. *Journal of Organic Chemistry* 2007, 72, (5), 1818-1821. Isolated tetraalkylated products were identified by $^1$H NMR. Once complete, the reaction was cooled to room temperature before being added dropwise to stirred ether, to precipitate out the product and remove excess alkylating agent. The resulting suspension was filtered through a bed of Celite and the porphyrin was washed through with methanol. The methanol was removed on a rotary evaporator, and the residue was taken up in H$_2$O (40 ml) and washed with dichloromethane (3×100 ml). The aqueous layer was isolated and evaporated under reduced pressure to leave behind meso-tetrakis-2(N-(N-(2-methoxyethyl)acetamido)pyridyl porphyrin as a shiny purple solid in 75% yield.

$^1$H NMR (400 MHz, CD$_3$OD): δ2.2-2.9 (multiplets and singlets, 28H, NHCH$_2$CH$_2$OCH$_3$), δ5.1-5.6 (doublets and singlets, 8H, N$^+$CH$_2$), δ8.77 (m, 4H, N$^+$CHCH), 68.5-9.4 (br s, 8H, H$_{pyrrole}$), 69.0 (m, 4H, N$^+$CHCHCH), 89.15 (m, 4H, N$^+$CCH), 89.55 (m, 4H, N$^+$CH)

UV-Vis (H$_2$O) λ (log ε): 418 (5.37).

Synthesis of iron(III) chloride meso-tetrakis-2(N-(N-(2-methoxyethyl)acetamido)pyridyl porphyrin The iron metallation of meso-tetrakis-2(N-(N-(2-methoxyethyl)acetamido)pyridyl porphyrin was performed according to a literature procedure. Szabo, C.; Mabley, J. G.; Moeller, S. M.; Shimanovich, R.; Pacher, P.; Virag, L.; Soriano, F. G.; Van Duzer, J. H.; Williams, W.; Salzman, A. L.; Groves, J. T., Part I: Pathogenic Role of Peroxynitrite in the Development of Diabetes and Diabetic Vascular Complications: Studies with FP15, A Novel Potent Peroxynitrite Decomposition Catalyst. *Molecular Medicine* 2002, 8, (10), 571-580. Briefly, meso-tetrakis-2(N-(N-(2-methoxyethyl)acetamido)pyridyl porphyrin (0.065 g, 4.63×10$^{-5}$. mol) was dissolved in a 0.12 g/ml aqueous solution of ferrous ammonium sulfate hexahydrate (8 ml) and raised to reflux in an oil bath. Reaction progress was monitored by UV-Vis, watching the Soret band broaden and shift from λ=418 nm to λ=412 nm and 2 of the Q bands disappear. The reaction mixture was cooled, stirred with chloride ion exchange resin (0.4 g) at room temperature for 2 hours, and neutralized with saturated aqueous sodium bicarbonate. After sitting overnight, the suspension was filtered through a bed of Celite, and the filtrate was evaporated down under reduced pressure. The residue was chromatographed on Sephadex LH-20 in 1:1 methanol: water. The appropriate fractions were combined and the solvent evaporated under reduced pressure, to leave iron(III)

chloride meso-tetrakis-2(N-(N-(2-methoxyethyl)acetamido) pyridyl porphyrin as a shiny black solid in 89% yield.

UV-Vis (H$_2$O) λ (log ε): 412 (4.80)

Example 6

Preparation of low-spin dicyano Complex for NMR Characterization

To a solution of the high-spin chloride complex of iron(III) chloride meso-tetrakis-2-(N-(2-methoxy)ethyl)pyridyl porphyrin in D$_2$O, was added 10 eq of NaCN in D$_2$O.

$^1$H NMR (400 MHz, D$_2$O): δ2.8 (singlets, 12H, CH$_2$CH$_2$OCH3), δ3.2-3.6 (m, 8H, CH$_2$CH$_2$OCH$_3$), δ4.4-4.8 (m, 8H, N$^+$CH$_2$), δ8.2 (s, 8H, pyrrole), δ8.4 (m, 4H, N$^+$CHCH), δ8.8-9.1 (m, 8H, N$^+$CHCHCH and N$^+$CCH), δ9.2 (m, 4H, N$^+$CH).

Example 7

Evaluation of the peroxynitrite decomposition ability of iron(III) chloride meso-tetrakis-2(N-(N-(2-methoxyethyl)acetamido)pyridyl porphyrin Synthesis of peroxynitrite Peroxynitrite was synthesized from hydrogen peroxide and nitrous acid using an sp250i syringe pump by modification of published procedures. See, Shimanovich, R.; Groves, J. T., Mechanisms of Peroxynitrite Decomposition Catalyzed by FeTMPS, a Bioactive Sulfonated Iron Porphyrin. *Archives of Biochemistry and Biophysics* 2001, 387, (2), 307-317; Saha, A.; Goldstein, S.; Cabelli, D.; Czapski, G., Determination of optimal conditions for synthesis of peroxynitrite by mixing acidified hydrogen peroxide with nitrite. *Free Radical Biology & Medicine* 1998, 24, (4), 653-659; and Uppu, R. M.; Squadrito, G. L.; Cueto, R.; Pryor, W. A., Selecting the most appropriate synthesis of peroxynitrite. *Methods in Enzymology* 1996, 269, 285-296; Koppenol, W. H.; Kissner, R.; Beckman, J. S., Syntheses of peroxynitrite: To go with the flow or on solid grounds? *Nitric Oxide, Part B* 1996, 269, 296-302. All reagents for peroxynitrite synthesis and analysis were degassed with argon thoroughly before use, and the synthesis was conducted under an argon atmosphere. Remaining hydrogen peroxide was reduced to less than 5% (molar ratio) of peroxynitrite with manganese dioxide (10 mg/ml at 4° C. for 30 min); MnO$_2$ was removed through 0.2 μm Supor membrane syringe filter (PALL). Peroxynitrite concentrations were determined spectrophotometrically at 302 nm (ε$_{302}$=1670 L mol$^{-1}$ cm$^{-1}$). Koppenol, W. H.; Kissner, R.; Beckman, J. S., Syntheses of peroxynitrite: To go with the flow or on solid grounds? *Nitric Oxide, Part B* 1996, 269, 296-302. In this manner, the concentration of peroxynitrite was determined to be 95 mM. The nitrite and nitrate content in peroxynitrite were estimated by ion chromatography on a Hamilton PRP X-100 anion-exchange column (125×4 mm), with 2.5% methanol in p-hydroxybenzoic acid (4.0 mM, pH 8.9) as eluent (1 ml/min). Nitrite and nitrate anions were detected and quantified by measuring the absorbance decrease (indirect UV detection) at 310 nm. Walker, T. A.; Ho, T. V.; Akbari, N., The isocratic separation and indirect UV detection of inorganic anions and mono-carboxylic and di-carboxylic acids on a low-capacity anion-exchange column. *Journal of Liquid Chromatography* 1991, 14, (7), 1351-1366. The concentration of nitrite was found to be 55 mM, and that of nitrate was 50 mM. Peroxynitrite was decomposed in 0.14 M HClO$_4$ prior to HPLC determination. Kissner, R.; Koppenol, W. H., Product distribution of peroxynitrite decay as a function of pH, temperature, and concentration. *Journal of the American Chemical Society* 2002, 124, (2), 234-239. Concentrations of hydrogen peroxide in the peroxynitrite before and after treatment with MnO$_2$ were measured by PeroXOquant Quantitative peroxide assay kit (Pierce Biotechnology), an assay based on the oxidation of Fe$^{2+}$ to Fe$^{3+}$ by H$_2$O$_2$ under acidic conditions. H$_2$O$_2$ measurements were performed after first decomposing peroxynitrite in phosphate buffer (0.5 M, pH 7.2). The concentration of remaining H$_2$O$_2$ in the peroxynitrite stock after MnO$_2$ treatment was 4 mM. Peroxynitrite solutions were prepared by diluting the stock solution immediately before use with 0.01 M NaOH to achieve the required concentrations.

Stopped-flow spectrophotometric analysis of kinetics of peroxynitrite decomposition by iron(III) chloride meso-tetrakis-2(N-(N-(2-methoxyethyl)acetamido)pyridyl porphyrin Iron(III) chloride meso-tetrakis-2(N-(N-(2-methoxyethyl) acetamido)pyridyl porphyrin, the test porphyrin, was reacted with peroxynitrite in a stopped-flow spectrophotometer in single-mixing experiments using single-wavelength mode, as we have previously described. Lee, J.; Hunt, J. A.; Groves, J. T., Mechanisms of Iron Porphyrin Reactions with Peroxynitrite. *J. Am. Chem. Soc.* 1998, 120, (30), 7493-7501. All reactions were carried out in 100 mM phosphate buffer at pH 7.4 and 25° C. by observing changes in the peroxynitrite absorbance at 302 nm. The concentration of iron(III) chloride meso-tetrakis-2(N-(N-(2-methoxyethyl)acetamido)pyridyl porphyrin was varied, and the post-mixing concentration of peroxynitrite was 63 M.

| [test porphyrin] (μM) | $t_{1/2}$ (s) |
|---|---|
| 5.15 | 0.038 |
| 6.18 | 0.024 |
| 7.21 | 0.018 |
| 8.24 | 0.011 |
| 9.27 | 0.0087 |
| 10.3 | 0.0078 |

| Catalyst | $k_{cat}$ (M$^{-1}$ s$^{-1}$) |
|---|---|
| Test porphyrin | 1.4 × 10$^7$ |
| FP15[2] | 7.6 × 10$^6$ |

Other Embodiments

It is to be understood that while the invention has been described in conjunction with the detailed description thereof, the foregoing description is intended to illustrate and not limit the scope of the invention, which is defined by the scope of the appended claims. For example, substituted-pyridyl derivatives, particularly those including PEG substituents, are particularly advantageous as peroxynitrite decomposition catalysts. Other aspects, advantages, and modifications are within the scope of the following claims.

What is claimed is:

1. A compound having the Formula I:

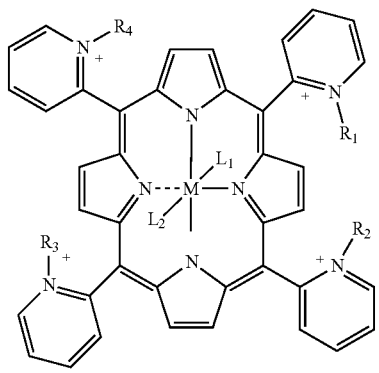

(I)

or a pharmaceutically acceptable base or acid addition salt, hydrate, ester, solvate, or stereoisomer, or mixtures thereof, wherein at least one of $R_1$, $R_2$, $R_3$, and $R_4$ is independently selected from the group consisting of $CH_2C(O)NR_5R_6$ and $(CH_2CH_2O)_tCH_3$, wherein t is 1, 2, 4, 5, 6, 7, 8, 9, or 10, and the remaining $R_1$, $R_2$, $R_3$, and $R_4$ are hydrogen;

$R_5$ and $R_6$ are selected from the group consisting of
H,
$CH_2CH_2OCH_3$,
$CH_2CH_2OCH_2CH_2OCH_3$,
$CH_2CH_2OCH_2CH_2OCH_2CH_2OCH_3$,
$CH_2COO^-$,
$(CH_2)_n—X$,
$(CH_2)_n—Y$,
$(CH_2)_nR_9—X$,
$(CH_2)_nR_9—Y$,
$CH_2CO_2CH_2CH_3$,
$(OCH_2CH_2)_m—X$,
$(OCH_2CH_2)_m—Y$,
$Y_2—X$,
$Y_2C(Z_1)_3$,
further wherein: $Z_1$ is $CH_2OCH_2(CH_2)_nX$ or $CH_2OCH_2(CH_2)_nY$;
$(CH_2)_nC(O)Y_2C(Z_2)_3$,
wherein: $Z_2$ is $CH_2OCH_2CH_2C(O)Y_2C(Z_4)_3$ and $Z_4$ is $CH_2OCH_2CH_2X$;
$(CH_2)_nC(O)—Y_2—C(Z_5)_3$,
wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$;
$(CH_2)_nOCH_2C(CH_2OH)_3$,
$(CH_2)_nOCH_2CH(CH_2OH)_2$,
$(CH_2)_nOCH_2C(CH_2OH)_2(CH_3)$,
$(CH_2)_nOCH_2C[CH_2OCH_2C(CH_2OH)_3]_3$,
$(CH_2)_nOCH_2C[CH_2OCH_2C(CH_2O[CH_2CH_2O]_mCH_2CH_2OX)_3]_3$,
$CH_2CONH—Y$,
$CH_2CO—Y$,
$CH_2CO(CH_2)_p—Y$;
alkyl,
cycloalkyl, and
aralkyl;
wherein n is an integer selected from 1, 2, 3, 4, 5, 6, 7, 8, 9, and 10; m is an integer from 1 to 200, and p is 1 or 2;

X is COOH, COOR', CONH$_2$, CONHR', CONR'$_2$, CO(CH$_2$)$_p$R', OPO$_3$H$_2$, PO$_3$H$_2$, SO$_3$H, NH$_2$, NR'$_2$, or NR'$_3^+$, a steroid, an amino acid, an oligosaccharide, a peptide, or a polycarboxylic acid, further wherein R' is alkyl, $CH_2CH_2OCH_3$, $CH_2CH_2OCH_2CH_2$ $OCH_3$, $(CH_2)_n—X$, $(CH_2)_n—Y$, $(CH_2)_nAr—X$, $(CH_2)_nAr—Y$, $CH_2CH_2OCH_2CH_2OCH_2CH_2OCH_3$, $CH_2CO_2CH_2CH_3$, $(OCH_2CH_2)_m—X$, $(OCH_2CH_2)_m—Y$, $Y_2—X$, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)—Y_2—C(Z_5)_3$, wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$,
$(CH_2)_nOCH_2C[CH_2OCH_2C(CH_2OH)_3]_3$,
$(CH_2)_nOCH_2C[CH_2OCH_2C(CH_2O[CH_2CH_2O]_mCH_2CH_2OX)_3]_3$, $CH_2CONH—Y$, $CH_2CO—Y$, and $CH_2CO(CH_2)_p—Y$;

Y is OH or $(OCH_2CH_2)_m—W_1$ or $(CH_2CH_2)_m—W_2$; where $W_1$ is OH, or $(OCH_2CH_2)_mOH$ and $W_2$ is OR", further wherein R" is an alkyl group;

$Y_2$ is selected from the group consisting of $(CH_2)_nO$, $(CH_2)_nNH$, and $(CH_2)_nS$, $CH_2CONH$, $CH_2COO$, or $CH_2CO(CH_2)_p$;

$R_9$ is substituted phenyl, unsubstituted phenyl, substituted napthyl, or unsubstituted naphthyl;

$L_1$ and $L_2$ are, independently, absent, halide, oxo, OH$_2$, hydroxo, CN, OPO$_3$H or alcohol; and M is absent, Mn or Fe;

provided that $R_5$ and $R_6$ are not both alkyl.

2. The compound of claim 1, wherein $R_1$, $R_2$, $R_3$, and $R_4$ are each $CH_2C(O)NR_5R_6$.

3. The compound of claim 1, wherein one of $R_5$ or $R_6$ is H.

4. The compound of claim 1, wherein one of $R_5$ or $R_6$ is selected from aralkyl, alkyl, cycloalkyl, substituted cycloalkyl, and $CH_2CH_2OCH_3$.

5. The compound of claim 4, wherein aralkyl is $(CR_7R_8)_s—R_9$, wherein $R_7$ and $R_8$ are, independently, selected from H, alkyl, OH, and halogen, and s is 1, 2, 3, 4, 5, 6, 7, 8, 9, or 10.

6. The compound of claim 5, wherein aralkyl is

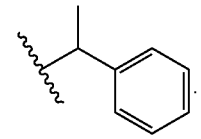

7. The compound of claim 4, wherein one of $R_5$ or $R_6$ is selected from alkyl, cycloalkyl, or substituted cycloalkyl.

8. The compound of claim 7, wherein cycloalkyl or substituted cycloalkyl is a bicyclic ring system.

9. The compound of claim 8, wherein the bicyclic ring system is bicycle[2.2.1]heptane.

10. The compound of claim 8, wherein the bicyclic ring system is 1,7,7-trimethylbicyclo[2.2.1]heptane.

11. The compound of claim 4, wherein one of $R_5$ or $R_6$ is $CH_2CH_2OCH_3$.

12. The compound of claim 1, wherein $R_1$, $R_2$, $R_3$, and $R_4$ are $(CH_2CH_2O)_tCH_3$.

13. The compound of claim 1, wherein t=1.

14. The compound of claim 1, wherein the compound is an ααββ atropisomer.

15. The compound of claim 1, wherein the compound is selected from

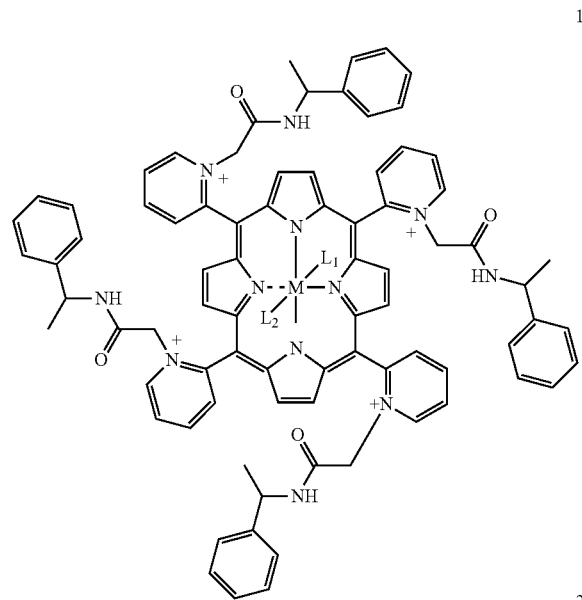

1

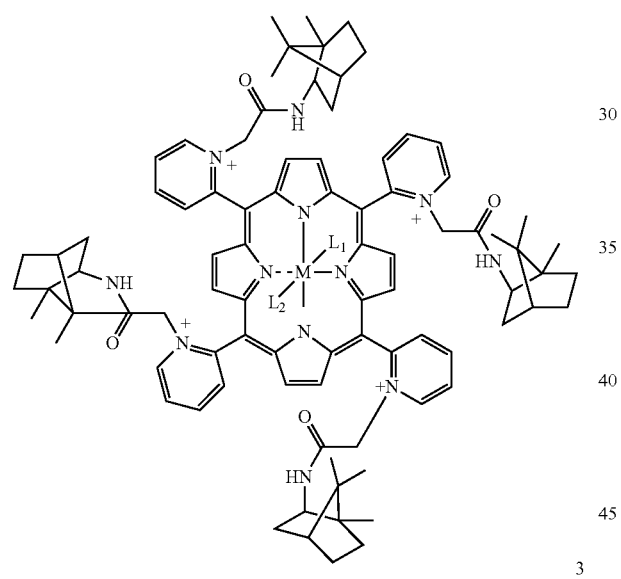

2

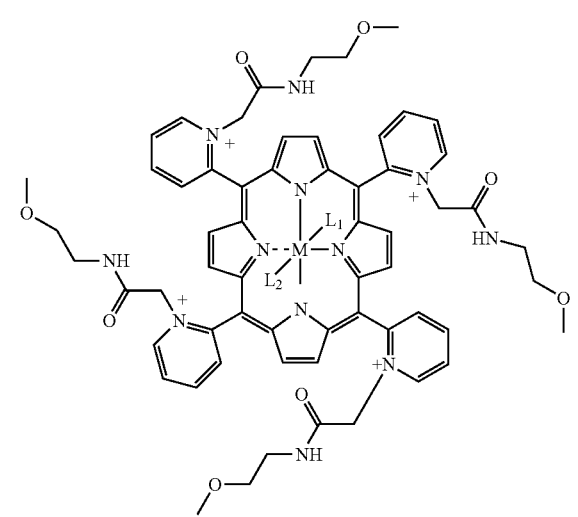

3

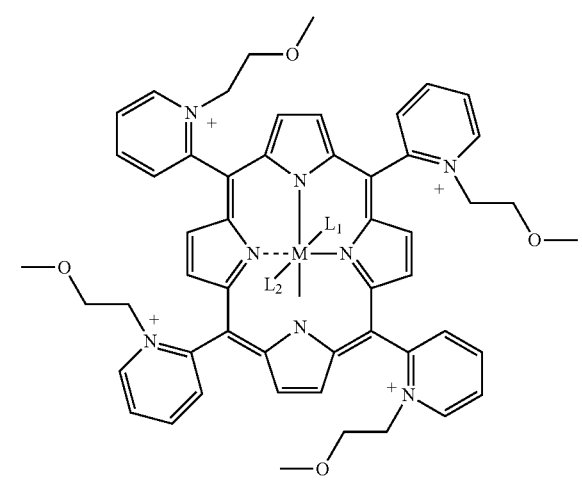

4 wherein $L_1$ and $L_2$ are, independently, absent, halide, oxo, $OH_2$, hydroxo, CN, $OPO_3H$ or alcohol; and M is absent, Mn or Fe.

16. A pharmaceutical composition comprising the compound of claim 1 and a pharmaceutically acceptable carrier.

17. A method of lowering peroxynitrite levels in a cell or tissue, the method comprising contacting said cell or tissue with a compound of Formula I in an amount sufficient to lower peroxynitrite levels in said cell or tissue:

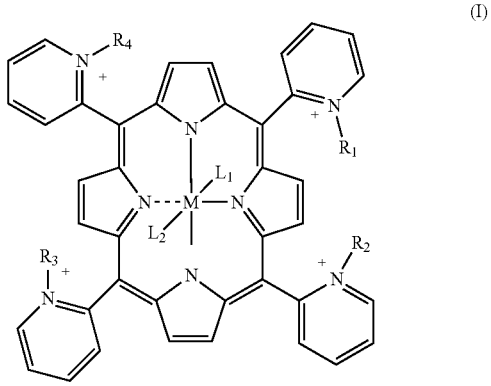

(I)

or a pharmaceutically acceptable base or acid addition salt, hydrate, ester, solvate, or stereoisomer, or mixtures thereof, wherein
at least one of $R_1$, $R_2$, $R_3$, and $R_4$ is independently selected from the group consisting of $CH_2C(O)NR_5R_6$ and $(CH_2CH_2O)_tCH_3$, wherein t is 1, 2, 4, 5, 6, 7, 8, 9, or 10, and the remaining $R_1$, $R_2$, $R_3$, and $R_4$ are hydrogen;
$R_5$ and $R_6$ are selected from the group consisting of
H,
$CH_2CH_2OCH_3$,
$CH_2CH_2OCH_2CH_2OCH_3$,
$CH_2CH_2OCH_2CH_2OCH_2CH_2OCH_3$,
$CH_2COO^-$,
$(CH_2)_n-X$,
$(CH_2)_n-Y$,
$(CH_2)_nR_9-X$,
$(CH_2)_nR_9-Y$,
$CH_2CO_2CH_2CH_3$,
$(OCH_2CH_2)_m-X$, $(OCH_2CH_2)_m—Y$,
$Y_2—X$,
$Y_2C(Z_1)_3$,
  further wherein: $Z_1$ is $CH_2OCH_2(CH_2)_nX$ or $CH_2OCH_2(CH_2)_nY$; $(CH_2)_nC(O)Y_2C(Z_2)_3$,
  wherein: $Z_2$ is $CH_2OCH_2CH_2C(O)Y_2C(Z_4)_3$ and $Z_4$ is $CH_2OCH_2CH_2X$; $(CH_2)_nC(O)—Y_2—C(Z_5)_3$,
  wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$;
$(CH_2)_nOCH_2C(CH_2OH)_3$,
$(CH_2)_nOCH_2CH(CH_2OH)_2$,
$(CH_2)_nOCH_2C(CH_2OH)_2(CH_3)$,
$(CH_2)_nOCH_2C[CH_2OCH_2C(CH_2OH)_3]_3$,
$(CH_2)_nOCH_2C[CH_2OCH_2C(CH_2O[CH_2CH_2O]_mCH_2CH_2OX)_3]_3$,
$CH_2CONH—Y$,
$CH_2CO—Y$,
$CH_2CO(CH_2)_p—Y$;
alkyl,
cycloalkyl, and
aralkyl;
wherein n is an integer selected from 1, 2, 3, 4, 5, 6, 7, 8, 9, and 10; m is an integer from 1 to 200, and p is 1 or 2;

X is COOH, COOR', $CONH_2$, CONHR', $CONR'_2$, $CO(CH_2)_pR'$, $OPO_3H_2$, $PO_3H_2$, $SO_3H$, $NH_2$, $NR'_2$, or $NR'_3{}^+$, a steroid, an amino acid, an oligosaccharide, a peptide, or a polycarboxylic acid, further wherein R' is alkyl, $CH_2CH_2OCH_3$, $CH_2CH_2OCH_2CH_2OCH_3$, $(CH_2)_n—X$, $(CH_2)_n—Y$, $(CH_2)_nAr—X$, $(CH_2)_nAr—Y$, $CH_2CH_2OCH_2CH_2OCH_2CH_2OCH_3$, $CH_2CO_2CH_2CH_3$, $(OCH_2CH_2)_m—X$, $(OCH_2CH_2)_m—Y$, $Y_2—X$, $Y_2C(Z_1)_3$, further wherein: $Z_1$ is $CH_2OCH_2(CH_2)_nX$ or $CH_2OCH_2(CH_2)_nY$; $(CH_2)_nC(O)Y_2C(Z_2)_3$, wherein: $Z_2$ is $CH_2OCH_2CH_2C(O)Y_2C(Z_4)_3$ and $Z_4$ is $CH_2OCH_2CH_2X$; $(CH_2)_nC(O)—Y_2—C(Z_5)_3$, wherein: $Z_5$ is $CH_2OCH_2CH_2C(O)Y_2C(Z_6)_3$ and $Z_6$ is $CH_2OCH_2CH_2C(O)O(CH_2CH_2O)_mCH_2CH_2O^-$; $(CH_2)_nOCH_2C(CH_2OH)_3$, $(CH_2)_nOCH_2CH(CH_2OH)_2$, $(CH_2)_nOCH_2C(CH_2OH)_2(CH_3)$, $(CH_2)_nOCH_2C[CH_2OCH_2C(CH_2OH)_3]_3$, $(CH_2)_nOCH_2C[CH_2OCH_2C(CH_2O[CH_2CH_2O]_mCH_2CH_2OX)_3]_3$, $CH_2CONH—Y$, $CH_2CO—Y$, and $CH_2CO(CH_2)_p—Y$;

Y is OH or $(OCH_2CH_2)_m—W_1$ or $(CH_2CH_2)_m—W_2$; where $W_1$ is OH, or $(OCH_2CH_2)_mOH$ and $W_2$ is OR", further wherein R" is an alkyl group;

$Y_2$ is selected from the group consisting of $(CH_2)_nO$, $(CH_2)_nNH$, and $(CH_2)_nS$, $CH_2CONH$, $CH_2COO$, or $CH_2CO(CH_2)_p$;

$R_9$ is substituted phenyl, unsubstituted phenyl, substituted napthyl, or unsubstituted naphthyl;

$L_1$ and $L_2$ are, independently, absent, halide, oxo, $OH_2$, hydroxo, CN, $OPO_3H$ or alcohol; and M is absent, Mn or Fe;

provided that $R_5$ and $R_6$ are not both alkyl.

* * * * *